US011618789B2

(12) United States Patent
Härtle

(10) Patent No.: US 11,618,789 B2
(45) Date of Patent: Apr. 4, 2023

(54) CLINICAL ASSESSMENT OF M-PROTEIN RESPONSE IN MULTIPLE MYELOMA

(71) Applicant: MORPHOSYS AG, Planegg (DE)

(72) Inventor: Stefan Härtle, Mammendorf (DE)

(73) Assignee: MORPHOSYS AG, Planegg (DE)

( * ) Notice: Subject to any disclaimer, the term of this patent is extended or adjusted under 35 U.S.C. 154(b) by 373 days.

(21) Appl. No.: 16/080,870

(22) PCT Filed: Mar. 3, 2017

(86) PCT No.: PCT/EP2017/055011
§ 371 (c)(1),
(2) Date: Aug. 29, 2018

(87) PCT Pub. No.: WO2017/149122
PCT Pub. Date: Sep. 8, 2017

(65) Prior Publication Data
US 2019/0077875 A1    Mar. 14, 2019

(30) Foreign Application Priority Data

Mar. 4, 2016   (EP) ..................... 16158714

(51) Int. Cl.
| | |
|---|---|
| *C07K 16/42* | (2006.01) |
| *C07K 16/18* | (2006.01) |
| *C07K 16/30* | (2006.01) |
| *G01N 33/574* | (2006.01) |
| *A61P 35/00* | (2006.01) |
| *C07K 14/76* | (2006.01) |
| *G01N 33/49* | (2006.01) |
| *G01N 33/561* | (2006.01) |

(52) U.S. Cl.
CPC .............. *C07K 16/30* (2013.01); *A61P 35/00* (2018.01); *C07K 14/76* (2013.01); *C07K 16/42* (2013.01); *G01N 33/49* (2013.01); *G01N 33/561* (2013.01); *G01N 33/57426* (2013.01); *C07K 2317/56* (2013.01); *C07K 2317/565* (2013.01); *C07K 2319/31* (2013.01); *G01N 2800/52* (2013.01)

(58) Field of Classification Search
CPC ................................ G01N 33/53; C07K 16/30
See application file for complete search history.

(56) References Cited

U.S. PATENT DOCUMENTS

| | | | | |
|---|---|---|---|---|
| 3,912,610 A | * | 10/1975 | Lou ...................... | G01N 27/447 436/516 |
| 4,102,990 A | * | 7/1978 | Uzgiris ................ | G01N 33/561 204/549 |
| 4,578,350 A | * | 3/1986 | Armenta .............. | G01N 33/535 435/188 |
| 4,661,586 A | | 4/1987 | Levy et al. ................... | 530/387 |
| 6,939,464 B1 | | 8/2005 | Zhu et al. .................... | 435/320.1 |
| 7,829,673 B2 | | 11/2010 | de Weers et al. .......... | 530/387.1 |
| 8,088,896 B2 | | 1/2012 | Tesar et al. ................. | 530/387.1 |
| 8,153,765 B2 | | 4/2012 | Park et al. .................. | 530/387.3 |
| 8,263,746 B2 | | 9/2012 | Tesar et al. ................. | 530/387.9 |
| 8,362,211 B2 | | 1/2013 | Elias et al. .................. | 530/387.1 |
| 9,102,744 B2 | | 8/2015 | Elias et al. | |
| 9,249,226 B2 | | 2/2016 | de Weers et al. | |
| 2002/0164788 A1 | | 11/2002 | Ellis et al. ..................... | 435/328 |
| 2008/0066741 A1 | * | 3/2008 | LeMahieu ............. | A61M 15/00 128/200.21 |
| 2008/0076117 A1 | * | 3/2008 | Herman ................ | C12Q 1/6886 435/6.14 |
| 2009/0123950 A1 | | 5/2009 | Tesar ........................... | 435/7.23 |
| 2009/0130089 A9 | * | 5/2009 | Smith ..................... | A61P 17/06 424/130.1 |
| 2011/0268726 A9 | * | 11/2011 | Tesar ........................ | A61P 7/00 424/133.1 |
| 2013/0302318 A1 | * | 11/2013 | Rojkjaer ................ | A61K 38/05 424/133.1 |
| 2015/0118251 A1 | | 4/2015 | Deslandes et al. ........ | 424/172.1 |

FOREIGN PATENT DOCUMENTS

| | | |
|---|---|---|
| JP | 2008-504221 | 2/2008 |
| JP | 2013-542191 | 11/2013 |
| JP | 2014-504850 | 2/2014 |
| JP | 2014-509187 | 4/2014 |
| WO | WO 99/62526 | 12/1999 |
| WO | WO 02/06347 | 1/2002 |
| WO | 2005/061546 | 7/2005 |
| WO | WO 05/103083 | 11/2005 |
| WO | WO 06/99875 | 9/2006 |
| WO | WO 06/125640 | 11/2006 |
| WO | WO 07/42309 | 4/2007 |
| WO | WO 08/47242 | 4/2008 |
| WO | WO2009/032128 | * 3/2009 |
| WO | WO 11/154453 | 12/2011 |
| WO | 2012/041800 | 4/2012 |
| WO | 2012/044612 | 4/2012 |
| WO | 2012/092616 | 7/2012 |
| WO | WO 12/92612 | 7/2012 |
| WO | WO 14/48921 | 4/2014 |
| WO | WO 14/178820 | 11/2014 |
| WO | WO 15/66450 | 5/2015 |
| WO | WO 15/121454 | 8/2015 |

OTHER PUBLICATIONS

Paul (Fundamental Immunology, 3rd Edition, 1993, pp. 292-295) (Year: 1993).*
Rudikoff et al. (Proceedings of the National Academy of Sciences USA, vol. 79, p. 1979-1983, 1982) (Year: 1982).*
HT Staff (Hematology Times, 2018) (Year: 2018).*
Sanofi (NCT01084252, 2010) (Year: 2010).*
Gimsing (Blood, vol. 118, No. 21, p. 817, 2011) (Year: 2011).*
Raab (Blood, vol. 126, No. 23, p. 3035, 2015) (Year: 2015).*
Communication pursuant to Article 94 (3) EPC in EP Application 17 708 766.5 dated Oct. 14, 2019.

(Continued)

*Primary Examiner* — Michael Allen
(74) *Attorney, Agent, or Firm* — Licata & Tyrrell P.C.

(57) ABSTRACT

Applicant discloses an anti-idiotypic antibody to MOR202, which when fused to human albumin, shifted the anti-body in IFE thus mitigating any potential interference of MOR202 with the M-protein clinical assessment.

6 Claims, 9 Drawing Sheets

Specification includes a Sequence Listing.

(56) References Cited

OTHER PUBLICATIONS

Chapter 2 "The Albumin Molecule: Its Structure and Chemical Properties" from Peters, T., Jr. (1996) All about Albumin: Biochemistry, Genetics and Medical, Applications pp. 10, Academic Press, Inc., Orlando pp. 9-75 and Figs 2-7, 2-8, 2-11 and 2-13.

Axel et al. "Development of a Clinical Assay to Mitigate Daratumumab, an IgG1κ Monoclonal Antibody, Interference with Serum Immunofixation (IFE) and Clinical Assessement of M-protein Response in Multiple Myeloma" Poster Presented at the 105th Annual Meeting of the American Association for Cancer Research (AACR), Apr. 5-9, 2014, San Diego, California, USA.

Genzen et al. "Detection of a monoclonal antibody therapy (ofatumumab) by serumprotein and immunofixation electrophoresis" British Journal of Haematology 2011 155(1):123-125.

McCudden et al. "Interference of Monclonal Antibody Therapies with Serum Protein Electrophoresis Tests" Clinical Chemistry 2010 56(12) 1897-1904.

Van de Donk et al. "Monoclonal antibodies targeting CD38 in hematological malignancies and beyond" Immunological Reviews 2016 270:95-112.

Yazaki et al. "Biodistribution and tumor imaging of an anti-CEA single-chain antibody-albumin fusion protein" Nuclear Medicine and Biology 2008 35(2):151-15.

Extended Search Report in EP Application No. 16158714.2 dated Aug. 16, 2018.

International Search Report and Written Opinion in PCT/EP2017/055011 dated May 16, 2017.

International Preliminary Examination Report on Patentability in PCT/EP2017/055011 dated May 16, 2017.

\* cited by examiner

Figure 1

The amino acid sequence of the MOR202 Variable Heavy Domain is:

QVQLVESGGGLVQPGGSLRLSCAASGFTFSSYYMNWVRQAPGKGLEWVSGISGDPSNTYYADSVKGRFTISRDNSKNTLYLQMNSLRAEDTAVYYCARDLPLVYTGFAYWGQGTLVTVSS (SEQ ID NO: 7)

The amino acid sequence of the MOR202 Variable Light Domain is:

DIELTQPPSVSVAPGQTARISCSGDNLRHYYVYWYQQKPGQAPVLVIYGDSKRPSGIPERFSGSNSGNTATLTISGTQAEDEADYYCQTYTGGASLVFGGGTKLTVLGQ (SEQ ID NO: 8)

The amino acid sequence of the MOR202 HCDR1 as defined by an internal nomenclature is: GFTFSSYYMN (SEQ ID NO: 9)

The amino acid sequence of the MOR202 HCDR1 as defined by Kabat is: SYYMN (SEQ ID NO: 10)

The amino acid sequence of the MOR202 HCDR2 as defined by Kabat is: GISGDPSNTYYADSVKG (SEQ ID NO: 11)

The amino acid sequence of the MOR202 HCDR3 as defined by Kabat is: DLPLVYTGFAY (SEQ ID NO: 12)

The amino acid sequence of the MOR202 LCDR1 as defined by Kabat is: SGDNLRHYYVY (SEQ ID NO: 13)

The amino acid sequence of the MOR202 LCDR2 as defined by Kabat is: GDSKRPS (SEQ ID NO: 14)

The amino acid sequence of the MOR202 LCDR3 as defined by Kabat is: QTYTGGAS (SEQ ID NO:15)

Figure 2 A

The amino acid sequence of the antibody MOR09292 (an anti-Id to MOR202) human albumin fusion protein named MOR09292-VH-CH1_HSA_6His (MOR09292-hAlb)

The amino acid sequence of the MOR09292 Variable Heavy Domain is:
QVQLVQSGAEVKKPGESLKISCKGSGYSFSNYWISWVRQMPGKGLEWMGIIDPASSKTRY
SPSFQGQVTISADKSISTAYLQWSSLKASDTAMYYCARSRGAGMDYWGQGTLVTVSS
(SEQ ID NO:16)

The amino acid sequence of the MOR09292 Variable Light Domain is:
DIVLTQPPSVSGAPGQRVTISCTGSSSNIGAGYDVHWYQQLPGTAPKLLIYADNNRPSGVPD
RFSGSKSGTSASLAITGLQSEDEADYYCGSYDESSNSMVFGGGTKLTVLGQ (SEQ ID NO:17)

The amino acid sequence of the MOR09292 HCDR1 as defined by Kabat is: YSFSNYWIS (SEQ ID NO:18)

The amino acid sequence of the MOR09292 HCDR2 as defined by Kabat is: WMGIIDPASSKTRYSPSFQG (SEQ ID NO:19)

The amino acid sequence of the MOR09292 HCDR3 as defined by Kabat is: SRGAGMDY (SEQ ID NO:20)

The amino acid sequence of the MOR09292 LCDR1 as defined by Kabat is: TGSSSNIGAGYDVH (SEQ ID NO:21)

The amino acid sequence of the MOR09292 LCDR2 as defined by Kabat is: LLIYADNNRPS (SEQ ID NO:22)

The amino acid sequence of the MOR09292 LCDR3 as defined by Kabat is: GSYDESSNSM (SEQ ID NO:23)

Figure 2 B

The amino acid sequence of the antibody MOR09292 (an anti-Id to MOR202) human albumin fusion protein named MOR09292-VH-CH1_HSA_6His (MOR09292-hAlb) (contd)

Heavy Chain with albumin fusion (MOR09292-VH-CH1_HSA_6His) (MOR09292-hAlb heavy chain):

QVQLVQSGAEVKKPGESLKISCKGSGYSFSNYWISWVRQMPGKGLEWMGIIDPASSKTRY
SPSFQGQVTISADKSISTAYLQWSSLKASDTAMYYCARSRGAGMDYWGQGTLVTVSSAST
KGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKRVEPKSDIDAHKSEVAHRFKDLGEENFKAL
VLIAFAQYLQQCPFEDHVKLVNEVTEFAKTCVADESAENCDKSLHTLFGDKLCTVATLRETY
GEMADCCAKQEPERNECFLQHKDDNPNLPRLVRPEVDVMCTAFHDNEETFLKKYLYEIARR
HPYFYAPELLFFAKRYKAAFTECCQAADKAACLLPKLDELRDEGKASSAKQRLKCASLQKF
GERAFKAWAVARLSQRFPKAEFAEVSKLVTDLTKVHTECCHGDLLECADDRADLAKYICEN
QDSISSKLKECCEKPLLEKSHCIAEVENDEMPADLPSLAADFVESKDVCKNYAEAKDVFLGM
FLYEYARRHPDYSVVLLLRLAKTYETTLEKCCAAADPHECYAKVFDEFKPLVEEPQNLIKQN
CELFEQLGEYKFQNALLVRYTKKVPQVSTPTLVEVSRNLGKVGSKCCKHPEAKRMPCAEDY
LSVVLNQLCVLHEKTPVSDRVTKCCTESLVNRRPCFSALEVDETYVPKEFNAETFTFHADIC
TLSEKERQIKKQTALVELVKHKPKATKEQLKAVMDDFAAFVEKCCKADDKETCFAEEGKKLV
AASQAALGLVNSR
HHHHHH (SEQ ID NO:24)

Light Chain (MOR09292-hAlb):

DIVLTQPPSVSGAPGQRVTISCTGSSSNIGAGYDVHWYQQLPGTAPKLLIYADNNRPSGVPD
RFSGSKSGTSASLAITGLQSEDEADYYCGSYDESSNSMVFGGGTKLTVLGQPKAAPSVTLF
PPSSEELQANKATLVCLISDFYPGAVTVAWKADSSPVKAGVETTTPSKQSNNKYAASSYLSL
TPEQWKSHRSYSCQVTHEGSTVEKTVAPTECS (SEQ ID NO:25)

Figure 7
A) MOR09292 IgG1 - IgG staining
B) MOR09292 IgG1 - lambda staining
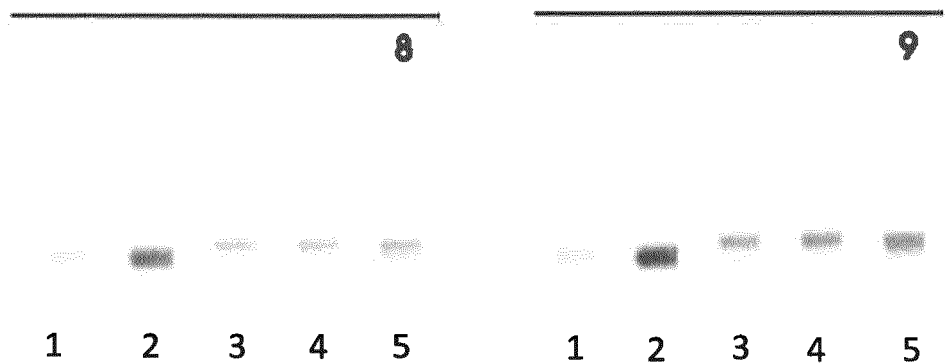
C) MOR09292 IgM – IgG, lamda and IgM staining
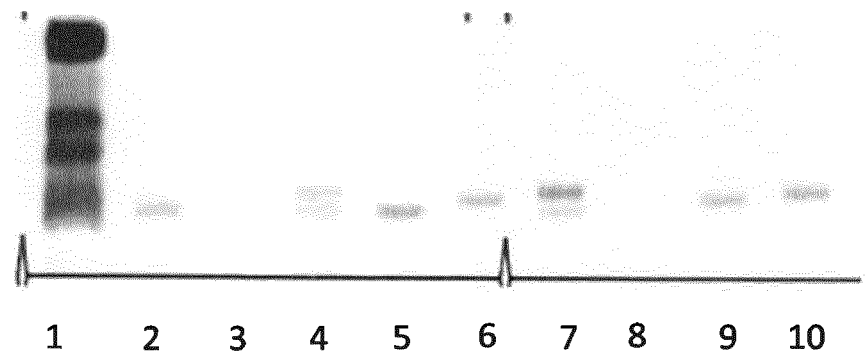

CLINICAL ASSESSMENT OF M-PROTEIN RESPONSE IN MULTIPLE MYELOMA

This patent application is the National Stage of International Application No. PCT/EP2017/055011 filed Mar. 3, 2017, which claims the benefit of EP 16158714.2 filed Mar. 4, 2016, each of which is incorporated by reference in its entirety.

BACKGROUND

Multiple myeloma (MM) is a hematological cancer that involves the clonal expansion of malignant plasma cells. MM is the most common malignant plasma cell tumor and the second most common hematologic malignancy in the United States. The US age-adjusted incidence rate is 5.5 cases per 100,000 and the annual incidence reaches approximately 6 to 7 per 100,000 in the United Kingdom.

Plasma cells produce immunoglobulins (also called gammaglobulins), which consist of a heavy chain (IgG, IgA, IgM, IgD or IgE) and a light chain (kappa or lambda) linked together. One plasma cell produces one type of immunoglobulin (for instance, IgA kappa or IgG kappa). Normally the body contains a variety of different plasma cells ("polyclonal"), thus the immunoglobulins in the serum also represent a broad spectrum of different formats and specificities (polyclonal). In the case of multiple myeloma, the malignant cells are copies of only one or only a few distinct plasma cell(s) and the Immunoglobulin secreted by this or these cell(s) is considered as monoclonal.

This monoclonal immunoglobulin is called M-protein or paraprotein and may also consist of a heavy chain (most often IgG or IgA but also IgM, IgD or IgE) and a light chain (kappa or lambda) or truncated forms of these immunoglobulins. The increase of M protein in the serum is used to identify B-cell malignancies, such as, MM.

Multiple staging systems are currently used for the diagnosis and monitoring of responses in multiple myeloma: a) the Durie and Salmon Staging System, b) the International Staging System (ISS), and the International Myeloma Working Group (IMWG). The Durie and Salmon staging system involves features that assess tumour cells mass, elevated serum immunoglobulin (Ig)G levels, end-organ damage, and osteolytic bone lesions. The ISS places more emphasis on the disease burden based on $\beta$2-microglobulin levels and serum albumin levels. The IMWG takes into account both molecular and cytogenetic abnormalities, specifically, M-protein reduction over time is one of the most important factors and is used to assess the progress of disease and treatment success.

Protein manifestations characteristic of multiple myeloma include increases of monoclonal (M)-protein concentrations (IgG, IgA, IgA, IgD), light chain concentrations (including kappa [$\kappa$] and lambda[$\lambda$]), abnormal $\beta$2-microglobulin, serum albumin, creatinine, and hemoglobin levels, and findings of bone marrow plasma cells (of greater than or equal to 5%). Measurement of the protein manifestations (such as M protein) produced by patients can be achieved by numerous methods. Tests that measure M-proteins are the 24-hour urine collection test, urine protein electrophoresis (UPEP), serum protein electrophoresis (SPEP), immunofixation electrophoresis (IFE), and serum free light chain (sFLC) assay.

CD38 is an example of an antigen expressed on malignant plasma cells, and other lymphocytes, and therefore, represents a therapeutic target in the treatment of multiple myeloma and other gammopathies. Functions ascribed to CD38 include both receptor mediation in adhesion and signaling events and (ecto-) enzymatic activity. As an ectoenzyme, CD38 uses NAD+ as substrate for the formation of cyclic ADP-ribose (cADPR) and ADPR, but also of nicotinamide and nicotinic acid-adenine dinucleotide phosphate (NAADP). cADPR and NAADP have been shown to act as second messengers for Ca2+ mobilization. By converting NAD+ to cADPR, CD38 regulates the extracellular NAD+ concentration and hence cell survival by modulation of NAD-induced cell death (NCID). In addition to signaling via Ca2+, CD38 signaling occurs via cross-talk with antigen-receptor complexes on T and B cells or other types of receptor complexes, e.g. MHC molecules, and is in this way involved in several cellular responses, but also in switching and secretion of IgG.

Antibodies specific for CD38 are in development for the treatment of multiple myeloma. Antibodies specific for CD38 are described in WO1999/62526 (Mayo Foundation); WO200206347 (Crucell Holland); US2002164788 (Jonathan Ellis) which is incorporated by reference in its entirety; WO2005/103083 (MorphoSys AG), U.S. Ser. No. 10/588,568, which is incorporated by reference in its entirety, WO2006/125640 (MorphoSys AG), U.S. Ser. No. 11/920,830, which is incorporated by reference in its entirety, and WO2007/042309 (MorphoSys AG), U.S. Ser. No. 12/089,806, which is incorporated by reference in its entirety; WO2006099875 (Genmab), U.S. Ser. No. 11/886,932, which is incorporated by reference in its entirety; WO2011154453A1 (Genmab), U.S. Ser. No. 13/702,857, which is incorporated by reference in its entirety; WO08/047242 (Sanofi-Aventis), U.S. Ser. No. 12/441,466, which is incorporated by reference in its entirety; WO2015066450 (Sanofi), U.S. Ser. No. 14/529,719, which is incorporated by reference in its entirety; WO2012092616A1, and WO2012092612A1 (Takeda), U.S. Ser. Nos. 13/341,860, and 13/977,207 both of which are incorporated by reference in their entirety, and WO2014178820A1 (Teva).

Anti-CD38 antibody treatment in MM patients can result in partial or complete clearance of the M-protein produced by multiple myeloma cells. Serum protein electrophoresis (SPEP) and immunofixation electrophoresis (IFE) are both essential assays used for identifying and immunotyping monoclonal proteins in patients with multiple myeloma. Recent studies demonstrated that certain therapeutic antibodies in development for the treatment of multiple myeloma are readily detected on serum IFE and can interfere with the detection and monitoring of M protein levels (McCudden et al., Clinical Chemistry, 56:12; 1897-1904 (2010), see also Genzen et al., British Journal of Haematology (2011) 155(1) 123-125). McCudden et al. observed that an incubation with Siltuximab (an anti-IL-6 antibody) with anti-drug antibodies shifted the drug electrophoretic pattern such that the therapeutic antibody Siltuximab could be differentiated from endogenous M-protein. Janssen also recently published the development of a clinical assay to mitigate Daratumumab's interference with M-protein in IFE using a similar approach, which utilized a mouse anti-daratumumab antibody ideally labeled with biotin or Alexafluor tags to shift the complex on IFE. Axel, et al., Development of a Clinical Assay to Mitigate Daratumumab, an IgG1k Monoclonal Antibody, Interference with Serum Immunofixation and Clinical Assessement of M-protein Response in Multiple Myeloma Poster Presented at the 105th Annual Meeting of the American Association for Cancer Research (AACR), Apr. 5-9, 2014, San Diego, Calif., USA; see also van de Donk et al., Monoclonal antibodies targeting CD38 in hematological malignancies and beyond, Immunological Reviews, 270:95-112 (2016).

These approaches, however, are not sufficient for every therapeutic antibody. Novel mitigation strategies are needed that are specific for each therapeutic antibody to avoid this potential interference with SPEP and IFE to ensure valid clinical response descriptions that meet the International Myeloma Working Group (IMWG) criteria.

SUMMARY OF THE INVENTION

Applicant herein discloses an anti-idiotypic antibody to MOR202, which when fused to human albumin, shifted the antibody in IFE thus mitigating any potential interference of MOR202 with the M-protein based clinical assessment.

The anti-idiotypic antibody, albumin fusion will be integrated into the clinical development design of MOR202 in order to enhance the clinical assessment of the M-protein response.

An aspect is an anti-idiotypic antibody to MOR202. In an aspect the anti-idiotypic antibody is fused to human albumin. In embodiments the anti-idiotypic antibody comprises a variable heavy chain comprising

```
an HCDR1 of the amino acid sequence
                                   (SEQ ID NO: 18)
YSFSNYWIS, an HCDR2 of the amino acid sequence
                                   (SEQ ID NO: 19)
WMGIIDPASSKTRYSPSFQG, an HCDR3 of the amino acid sequence
and a variable light chain comprising
                                   (SEQ ID NO: 20)
SRGAGMDY, an LCDR1 of the amino acid sequence
                                   (SEQ ID NO: 21)
TGSSSNIGAGYDVH, an LCDR2 of the amino acid sequence
                                   (SEQ ID NO: 22)
LLIYADNNRPS, an LCDR3 of the amino acid sequence
                                   (SEQ ID NO: 23)
GSYDESSNSM.
```

In an embodiment, the anti-idiotypic antibody is a human antibody.

In embodiments, the anti-idiotypic antibody fusion comprises the heavy chain of amino acid sequence

```
                                   (SEQ ID NO: 24)
QVQLVQSGAEVKKPGESLKISCKGSGYSFSNYWISWVRQMPGKGLEWMGI

IDPASSKTRYSPSFQGQVTISADKSISTAYLQWSSLKASDTAMYYCARSR

GAGMDYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKRVEPKSDIDAHKSEVAHRFKDLGEENFKALVLIAFAQ

YLQQCPFEDHVKLVNEVTEFAKTCVADESAENCDKSLHTLFGDKLCTVAT

LRETYGEMADCCAKQEPERNECFLQHKDDNPNLPRLVRPEVDVMCTAFHD

NEETFLKKYLYEIARRHPYFYAPELLFFAKRYKAAFTECCQAADKAACLL

PKLDELRDEGKASSAKQRLKCASLQKFGERAFKAWAVARLSQRFPKAEFA

EVSKLVTDLTKVHTECCHGDLLECADDRADLAKYICENQDSISSKLKECC

EKPLLEKSHCIAEVENDEMPADLPSLAADFVESKDVCKNYAEAKDVFLGM

FLYEYARRHPDYSVVLLLRLAKTYETTLEKCCAAADPHECYAKVFDEFKP

LVEEPQNLIKQNCELFEQLGEYKFQNALLVRYTKKVPQVSTPTLVEVSRN

LGKVGSKCCKHPEAKRMPCAEDYLSVVLNQLCVLHEKTPVSDRVTKCCTE

SLVNRRPCFSALEVDETYVPKEFNAETFTFHADICTLSEKERQIKKQTAL

VELVKHKPKATKEQLKAVMDDFAAFVEKCCKADDKETCFAEEGKKLVAAS

QAALGLVNSRHHHHHH.
```

In embodiments, the anti-idiotypic antibody fusion comprises the light chain of amino acid sequence

```
                                   (SEQ ID NO: 25)
DIVLTQPPSVSGAPGQRVTISCTGSSSNIGAGYDVHWYQQLPGTAPKLLI

YADNNRPSGVPDRFSGSKSGTSASLAITGLQSEDEADYYCGSYDESSNSM

VFGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS
```

An aspect is a method of evaluating a blood sample obtained from a patient undergoing treatment for multiple myeloma or other gammopathy comprising
  a) obtaining a blood sample from said patient,
  b) incubating the blood sample with an anti-idiotypic antibody,
  c) performing immunofixation electrophoresis (IFE), and
  d) reporting the results of the IFE.

In embodiments, the patient is undergoing treatment with MOR202.

In embodiments, the sample is evaluated for total M-protein levels.

An aspect, is a nucleic acid encoding the exemplified anti-idiotypic antibody or exemplified anti-idiotypic antibody albumin fusion.

DESCRIPTION OF DRAWINGS

FIG. 1 shows the amino acid sequence of MOR202.

FIGS. 2A-B show the amino acid sequence of MOR09292 (an anti-idiotypic antibody to MOR202) human albumin fusion protein.

FIG. 7 shows a serum immunofixation electrophoresis of MOR202+/−preincubation of MOR0929 IgG1 and MOR09292 IgM in saline. MOR202 at a constant concentration of 1200 µg/mL (A and B) or 560 µg/mL (C) in saline was pre-incubated with its idiotypic antibody MOR09292 in different formats and the prepared samples were analyzed via IFE. A)+B): MOR202 and MOR09292 IgG1 (using anti-IgG staining (A) and anti-lambda staining (B) (Lane 1=MOR202; Lane 2=MOR09292 IgG1 2400 µg/mL; Lane 3=MOR202+MOR09292 IgG1 at 600 µg/mL; Lane 4=MOR202+MOR09292 IgG1 at 1200 µg/mL; Lane 5=MOR202+MOR09292 IgG1 at 2400 µg/mL). C): MOR202 and MOR09292 IgM using anti-IgG staining (Lane 2-4), anti-lambda staining (Lane 5-7) and anti-IgM staining (Lane 8-10) (Lane 2/5/8=MOR202; Lane 3/6/9=MOR09292 IgM 560 µg/mL; Lane 4/7/10=MOR202+MOR09292 IgM 560 µg/mL; Lane 1=human serum from a healthy donor stained for total protein to evaluate general background signaling in serum samples).

Figure 8:
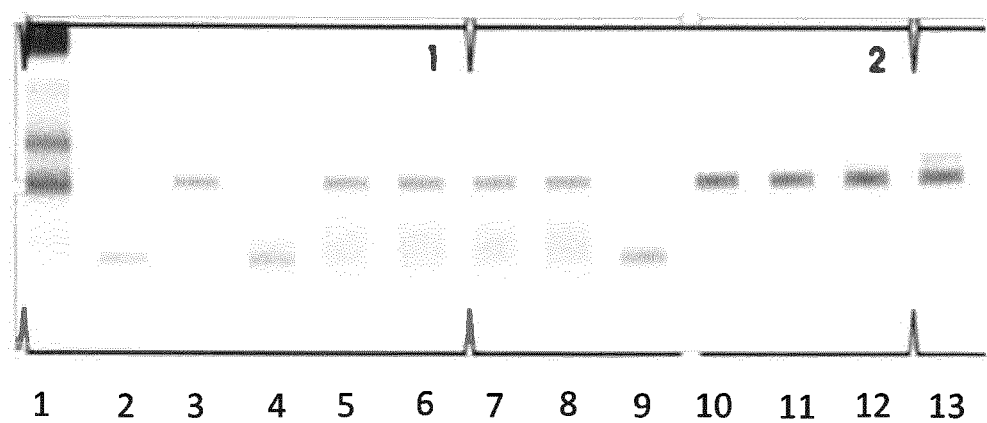

FIG. 8 shows a serum immunofixation electrophoresis of MOR202+/−preincubation of MOR09292-human albumin fusion (MOR09292-hAlb) in saline and human serum. MOR202 at a constant concentration of 1200 µg/mL in saline (Lane 2-3) or serum (Lane 4-13) was pre-incubated with or without its idiotypic antibody MOR09292-hAlb at different ratios and the prepared samples were analyzed via IFE using anti-IgG staining (Lane 2-8) or anti-lambda staining (Lane 9-13). (Lane 2=MOR202; Lane 3=MOR202+MOR09292-hAlb at 2400 µg/mL; Lane 4=MOR202; Lane 5=MOR202+MOR09292-hAlb at 1200 µg/mL; Lane 6=MOR202+MOR09292-hAlb at 1800 µg/mL; Lane 7=MOR202+MOR09292-hAlb at 2400 µg/mL; Lane 8=MOR202+MOR09292-hAlb at 3600 µg/mL; Lane 9=MOR202; Lane 10=MOR202+MOR09292-hAlb at 1200 µg/mL; Lane 11=MOR202+MOR09292-hAlb at 1800 µg/mL; Lane 12=MOR202+MOR09292-hAlb at 2400 µg/mL; Lane 13=MOR202+MOR09292-hAlb at 3600 µg/mL; Lane 1=human serum from a healthy donor stained for total protein to evaluate general background signaling).

DETAILED DESCRIPTION OF THE INVENTION

Definitions

The term "anti-idiotypic" describes a protein or peptide that binds to the variable regions of an antibody. The anti-idiotypic protein can be an antibody. For example, antibody MOR09292 binds to the variable regions of MOR202.

The term "antibody" includes antibody fragments. Antibodies include monoclonal antibodies of any isotype, e.g., IgG, IgM, IgA, IgD and IgE. An IgG antibody is comprised of two identical heavy chains and two identical light chains that are joined by disulfide bonds. The heavy and light chains of antibodies contain a constant region and a variable region. Each variable region contains three segments called "complementarity-determining regions" ("CDRs") or "hypervariable regions", which are primarily responsible for binding an epitope of an antigen. They are referred to as CDR1, CDR2, and CDR3, numbered sequentially from the N-terminus. The more highly conserved portions of the variable regions outside of the CDRs are called the "framework regions". An "antibody fragment" means an Fv, scFv, dsFv, Fab, Fab'F(ab')2 fragment, or other fragment, which contains at least one variable heavy or variable light chain, each containing CDRs and framework regions.

The "CDRs" herein are defined by either Chothia et al.., Kabat et al. or by an internal numbering convention. See Chothia C, Lesk A M. (1987) Canonical structures for the hypervariable regions of immunoglobulins. J Mol Biol., 196(4):901-17, which is incorporated by reference in its entirety. See Kabat E. A, Wu T. T., Perry H. M., Gottesman K. S. and Foeller C. (1991). Sequences of Proteins of Immunological Interest. 5th edit., NIH Publication no. 91-3242, US Dept. of Health and Human Services, Washington, D.C., which is incorporated by reference in its entirety.

"VH" refers to the variable region of an immunoglobulin heavy chain of an antibody, or antibody fragment. "VL" refers to the variable region of the immunoglobulin light chain of an antibody, or antibody fragment.

"Fc region" means the constant region of an antibody, which in humans may be of the IgG1, 2, 3, 4 subclass or others. The sequences of human Fc regions are available at IMGT, Human IGH C-REGIONs, http with the extension imgt.org/ligmdb/ of the world wide web(retrieved on 22 Feb. 2016).

A "human antibody" or "human antibody fragment", as used herein, includes antibodies and antibody fragments having variable regions in which both the framework and CDR regions are derived from sequences of human origin. Furthermore, if the antibody contains a constant region, the constant region also is derived from such sequences.

"Specific" describes a protein that recognizes an antigen and is able to discriminate between such antigen and one or more reference antigen(s). This ability can be identified by a standard ELISA assay. Typically, determination of specificity is performed by using not a single reference antigen, but a set of about three to five unrelated antigens, such as milk powder, BSA, transferrin or the like.

"Evaluating a blood sample" means evaluating the blood or portion of the blood sample most relevant for the method. Currently immunofixation electrophoresis is done on the serum component of blood. If, however, in the future a different blood component is evaluated, the invention is directed to a method evaluating that blood component. Blood components include, for example, plasma, serum, cells, e.g. red and white cells, and platelets. Plasma includes proteins, such as globulins, and clotting factors, and salts, sugars, fat, hormones and vitamins.

Gammopathies are conditions in which serum immunoglobulin levels are greatly increased. They can be classified either as polyclonal (increases in all major immunoglobulin classes) or monoclonal (increases in a single homogeneous immunoglobulin).

Polyclonal gammopathies result from chronic stimulation of the immune system. They can therefore be caused by chronic pyodermas; chronic viral, bacterial, or fungal infections; granulomatous bacterial diseases; abscesses; chronic parasitic infections; chronic rickettsial diseases, such as tropical canine pancytopenia; chronic immunologic diseases, such as systemic lupus erythematosus, rheumatoid arthritis, and myositis; or by some neoplasia. In many cases, there is no obvious predisposing cause. In some animals, the gammopathy may initially be monoclonal because of the predominance of a single immunoglobulin class (usually IgG).

Monoclonal gammopathies are characterized by the production of large amounts of a single immunoglobulin protein. Monoclonal gammopathies are either benign (ie, associated with no underlying disease), or more commonly, associated with immunoglobulin-secreting tumors. Tumors that secrete monoclonal antibodies originate from plasma cells (myelomas). Myelomas can secrete intact proteins of any immunoglobulin class or immunoglobulin subunits or fragments (light chains or heavy chains). Examples of Monoclonal gammopathies include: Hodgkin's disease; variants of multiple myeloma, e.g., Solitary plasmacytoma of bone, Extramedullary plasmacytoma, Plasma cell leukemia, and Non-secretory myeloma, Lymphoproliferative disorders, such as, Waldenstrom's macroglobulinemia, and Lymphoma; Heavy chain disease (γ, α, μ); and Amyloidosis.

The term "CD38" refers to the protein known as CD38, having the following synonyms: ADP-ribosyl cyclase 1, cADPr hydrolase 1, Cyclic ADP-ribose hydrolase 1, T10.

Human CD38 has the amino acid sequence of:

(SEQ ID NO: 1)
MANCEFSPVSGDKPCCRLSRRAQLCLGVSILVLILVVVLAVVVPRWRQQW

SGPGTTKRFPETVLARCVKYTEIHPEMRHVDCQSVWDAFKGAFISKHPCN

ITEEDYQPLMKLGTQTVPCNKILLWSRIKDLAHQFTQVQRDMFTLEDTLL

GYLADDLTWCGEFNTSKINYQSCPDWRKDCSNNPVSVFWKTVSRRFAEAA

CDVVHVMLNGSRSKIFDKNSTFGSVEVHNLQPEKVQTLEAWVIHGGREDS

RDLCQDPTIKELESIISKRNIQFSCKNIYRPDKFLQCVKNPEDSSCTS

EI.

"MOR202" an anti-CD38 antibody whose amino acid sequence is provided in FIG. 1. "MOR202" and "MOR03087" are used as synonyms to describe the antibody shown in FIG. 1.

The DNA sequence encoding the MOR202 Variable Heavy Domain is:

(SEQ ID NO: 2)
CAGGTGCAATTGGTGGAAAGCGGCGGCGGCCTGGTGCAACCGGGCGGCAG

CCTGCGTCTGAGCTGCGCGGCCTCCGGATTTACCTTTTCTTCTTATTATA

TGAATTGGGTGCGCCAAGCCCCTGGGAAGGGTCTCGAGTGGGTGAGCGGT

ATCTCTGGTGATCCTAGCAATACCTATTATGCGGATAGCGTGAAAGGCCG

TTTTACCATTTCACGTGATAATTCGAAAAACACCCTGTATCTGCAAATGA

ACAGCCTGCGTGCGGAAGATACGGCCGTGTATTATTGCGCGCGTGATCTT

CCTCTTGTTTATACTGGTTTTGCTTATTGGGGCCAAGGCACCCTGGTGAC

GGTTAGCTCA

The DNA sequence encoding the MOR202 Variable Light Domain is:

(SEQ ID NO: 3)
GATATCGAACTGACCCAGCCGCCTTCAGTGAGCGTTGCACCAGGTCAGAC

CGCGCGTATCTCGTGTAGCGGCGATAATCTTCGTCATTATTATGTTTATT

GGTACCAGCAGAAACCCGGGCAGGCGCCAGTTCTTGTGATTTATGGTGAT

TCTAAGCGTCCCTCAGGCATCCCGGAACGCTTTAGCGGATCCAACAGCGG

CAACACCGCGACCCTGACCATTAGCGGCACTCAGGCGGAAGACGAAGCGG

ATTATTATTGCCAGACTTATACTGGTGGTGCTTCTCTTGTGTTTGGCGGC

GGCACGAAGTTAACCGTTCTTGGCCAG

MOR202 is disclosed in WO2007/042309, U.S. Ser. No. 12/089,806, which is incorporated by reference in its entirety. In U.S. Ser. No. 12/089,806, MOR202 is the antibody comprising the variable heavy chain corresponding to SEQ ID NO: 21 and variable light chain corresponding to SEQ ID NO: 51, and the nucleic acids encoding MOR202 are variable heavy chain SEQ ID NO: 6 and variable light chain SEQ ID NO:36.

MOR202 is currently being tested in a phase ½a trial in patients with relapsed/refractory myeloma. The study is evaluating the safety and preliminary efficacy of MOR202 as monotherapy and in combination with pomalidomide and lenalidomide plus dexamethasone.

The antibody, MOR09292, is an anti-idiotypic antibody to MOR202 and is encoded by the nucleic acid sequence:

VH:
(SEQ ID NO: 4)
CAGGTGCAATTGGTTCAGAGCGGCGCGGAAGTGAAAAAACCGGGCGAAAG

CCTGAAAATTAGCTGCAAAGGTTCCGGATATTCCTTTTCTAATTATTGGA

TTTCTTGGGTGCGCCAGATGCCTGGGAAGGGTCTCGAGTGGATGGGCATT

ATCGATCCGGCTTCTAGCAAGACCCGTTATTCTCCGAGCTTTCAGGGCCA

GGTGACCATTAGCGCGGATAAAAGCATTAGCACCGCGTATCTTCAATGGA

GCAGCCTGAAAGCGAGCGATACGGCCATGTATTATTGCGCGCGTTCTCGT

GGTGCTGGTATGGATTATTGGGGCCAAGGCACCCTGGTGACGGTTAGCTC

A

VL:
(SEQ ID NO: 5)
GATATCGTGCTGACCCAGCCGCCTTCAGTGAGTGGCGCACCAGGTCAGCG

TGTGACCATCTCGTGTACGGGCAGCAGCAGCAACATTGGTGCTGGTTATG

ATGTGCATTGGTACCAGCAGTTGCCCGGGACGGCGCCGAAACTTCTGATT

TATGCTGATAATAATCGTCCCTCAGGCGTGCCGGATCGTTTTAGCGGATC

CAAAAGCGGCACCAGCGCGAGCCTTGCGATTACGGGCCTGCAAAGCGAAG

ACGAAGCGGATTATTATTGCGGTTCTTATGATGAGTCTTCTAATTCTATG

GTGTTTGGCGGCGGCACGAAGTTAACCGTTCTTGGCCAG

DNA encoding MOR09292-VH-CH1_HSA_6His (no leader sequence) (MOR09292-hAlb heavy chain):

(SEQ ID NO: 26)
CAGGTGCAATTGGTTCAGAGCGGCGCGGAAGTGAAAAAACCGGGCGAAAG

CCTGAAAATTAGCTGCAAAGGTTCCGGATATTCCTTTTCTAATTATTGGA

TTTCTTGGGTGCGCCAGATGCCTGGGAAGGGTCTCGAGTGGATGGGCATT

ATCGATCCGGCTTCTAGCAAGACCCGTTATTCTCCGAGCTTTCAGGGCCA

GGTGACCATTAGCGCGGATAAAAGCATTAGCACCGCGTATCTTCAATGGA

GCAGCCTGAAAGCGAGCGATACGGCCATGTATTATTGCGCGCGTTCTCGT

GGTGCTGGTATGGATTATTGGGGCCAAGGCACCCTGGTGACGGTTAGCTC

-continued

```
AGCCTCCACCAAGGGTCCATCGGTCTTCCCCCTGGCACCCTCCTCCAAGA
GCACCTCTGGGGGCACAGCGGCCCTGGGCTGCCTGGTCAAGGACTACTTC
CCCGAACCGGTGACGGTGTCGTGGAACTCAGGCGCCCTGACCAGCGGCGT
GCACACCTTCCCGGCTGTCCTACAGTCCTCAGGACTCTACTCCCTCAGCA
GCGTGGTGACCGTGCCCTCCAGCAGCTTGGGCACCCAGACCTACATCTGC
AACGTGAATCACAAGCCCAGCAACACCAAGGTGGACAAGAGAGTTGAGCC
CAAATCTGATATCGACGCCCACAAGAGCGAGGTGGCCCACCGGTTTAAGG
ACCTGGGCGAGGAAAACTTCAAGGCCCTGGTGCTGATCGCCTTCGCCCAG
TACCTGCAGCAGTGCCCCTTCGAGGACCACGTGAAGCTCGTGAACGAAGT
GACCGAGTTCGCCAAGACCTGCGTGGCCGATGAGAGCGCCGAGAACTGCG
ACAAGAGCCTGCACACCCTGTTCGGCGACAAGCTGTGTACCGTGGCCACC
CTGAGAGAAACCTACGGCGAGATGGCCGACTGCTGCGCCAAGCAGGAACC
CGAGAGGAACGAGTGCTTCCTGCAGCACAAGGACGACAACCCCAACCTGC
CCAGACTCGTGCGCCCGAAGTGGACGTGATGTGCACCGCCTTCCACGAC
AACGAGGAAACCTTCCTGAAGAAGTACCTGTACGAGATCGCCAGACGGCA
CCCCTACTTCTACGCCCCCGAGCTGCTGTTCTTCGCCAAGCGGTACAAGG
CCGCCTTCACCGAGTGTTGCCAGGCCGCCGATAAGGCCGCTTGCCTGCTG
CCTAAGCTGGACGAGCTGAGGGATGAGGGCAAGGCCAGCTCTGCCAAGCA
GAGACTGAAGTGCGCCAGCCTGCAGAAGTTCGGCGAGCGGGCCTTTAAAG
CCTGGGCCGTGGCTAGACTGAGCCAGAGATTCCCCAAGGCCGAGTTTGCC
GAGGTGTCCAAGCTCGTGACCGACCTGACCAAGGTGCACACCGAGTGCTG
TCACGGCGACCTGCTGGAATGCGCCGACGACAGAGCCGATCTGGCCAAGT
ACATCTGCGAGAACCAGGACAGCATCAGCAGCAAGCTGAAAGAGTGCTGC
GAGAAGCCTCTGCTGGAAAAGAGCCACTGTATCGCCGAGGTGGAAAACGA
CGAGATGCCCGCCGATCTGCCTTCTCTGGCCGCCGACTTCGTGGAAAGCA
AGGACGTGTGCAAGAACTACGCCGAGGCCAAGGATGTGTTCCTGGGCATG
TTTCTGTATGAGTACGCCCGCAGACACCCCGACTACAGCGTGGTGCTGCT
GCTGAGACTGGCCAAAACCTACGAGACAACCCTGGAAAAGTGCTGTGCCG
CCGCTGACCCCCACGAGTGTTACGCCAAGGTGTTCGACGAGTTCAAGCCA
CTGGTGGAAGAACCCCAGAACCTGATCAAGCAGAATTGCGAGCTGTTCGA
GCAGCTGGGCGAGTACAAGTTCCAGAACGCCCTGCTCGTGCGGTACACCA
AGAAAGTGCCCCAGGTGTCCACCCCCACCCTGGTGGAAGTGTCCCGGAAC
CTGGGCAAAGTGGGCAGCAAGTGCTGCAAGCACCCTGAGGCCAAGAGAAT
GCCCTGCGCCGAGGACTACCTGTCTGTGGTGCTGAACCAGCTGTGCGTGC
TGCACGAGAAAACCCCCGTGTCCGACAGAGTGACCAAGTGCTGTACCGAG
AGCCTCGTGAACAGACGGCCCTGCTTCAGCGCCCTGGAAGTGGATGAGAC
ATACGTGCCCAAAGAGTTCAACGCCGAGACATTCACCTTCCACGCCGACA
TCTGCACCCTGTCCGAGAAAGAGCGGCAGATCAAGAAACAGACCGCTCTG
GTGGAACTCGTGAAGCACAAGCCCAAGGCCACCAAAGAACAGCTGAAGGC
CGTGATGGACGACTTCGCCGCCTTTGTGGAAAAATGCTGCAAGGCCGATG
ACAAAGAGACATGCTTCGCCGAAGAGGGCAAGAAACTGGTGGCCGCCTCT
CAGGCTGCTCTGGGACTGGTTAACTCTAGACACCATCACCATCACCAT.
```

DNA encoding MOR09292-VL-lambda (no leader sequence) (MOR09292-hAlb light chain):

(SEQ ID NO: 27)
```
GATATCGTGCTGACCCAGCCGCCTTCAGTGAGTGGCGCACCAGGTCAGCG
TGTGACCATCTCGTGTACGGGCAGCAGCAGCAACATTGGTGCTGGTTATG
ATGTGCATTGGTACCAGCAGTTGCCCGGGACGGCGCCGAAACTTCTGATT
TATGCTGATAATAATCGTCCCTCAGGCGTGCCGGATCGTTTTAGCGGATC
CAAAAGCGGCACCAGCGCGAGCCTTGCGATTACGGGCCTGCAAAGCGAAG
ACGAAGCGGATTATTATTGCGGTTCTTATGATGAGTCTTCTAATTCTATG
GTGTTTGGCGGCGGCACGAAGTTAACCGTCCTAGGTCAGCCCAAGGCTGC
CCCCTCGGTCACTCTGTTCCCGCCCTCCTCTGAGGAGCTTCAAGCCAACA
AGGCCACACTGGTGTGTCTCATAAGTGACTTCTACCCGGGAGCCGTGACA
GTGGCCTGGAAGGCAGATAGCAGCCCCGTCAAGGCGGGAGTGGAGACCAC
CACACCCTCCAAACAAAGCAACAACAAGTACGCGGCCAGCAGCTATCTGA
GCCTGACGCCTGAGCAGTGGAAGTCCCACAGAAGCTACAGCTGCCAGGTC
ACGCATGAAGGGAGCACCGTGGAGAAGACAGTGGCCCCTACAGAATGTTC
A.
```

Human albumin has the following amino acid sequence (including the signal sequence):

(SEQ ID NO: 6)
MKWVTFISLLFLFSSAYSRGVFRRDAHKSEVAHRFKDLGEENFKALVLIA
FAQYLQQCPFEDHVKLVNEVTEFAKTCVADESAENCDKSLHTLFGDKLCT
VATLRETYGEMADCCAKQEPERNECFLQHKDDNPNLPRLVRPEVDVMCTA
FHDNEETFLKKYLYEIARRHPYFYAPELLFFAKRYKAAFTECCQAADKAA
CLLPKLDELRDEGKASSAKQRLKCASLQKFGERAFKAWAVARLSQRFPKA
EFAEVSKLVTDLTKVHTECCHGDLLECADDRADLAKYICENQDSISSKLK
ECCEKPLLEKSHCIAEVENDEMPADLPSLAADFVESKDVCKNYAEAKDVF
LGMFLYEYARRHPDYSVVLLLRLAKTYETTLEKCCAAADPHECYAKVFDE
FKPLVEEPQNLIKQNCELFEQLGEYKFQNALLVRYTKKVPQVSTPTLVEV
SRNLGKVGSKCCKHPEAKRMPCAEDYLSVVLNQLCVLHEKTPVSDRVTKC
CTESLVNRRPCFSALEVDETYVPKEFNAETFTFHADICTLSEKERQIKKQ
TALVELVKHKPKATKEQLKAVMDDFAAFVEKCCKADDKETCFAEEGKKLV
AASQAALGL

The International Myeloma Working Group (IMWG) Uniform Response Criteria for Multiple Myeloma are as follows:

| Response | IMWG criteria |
| --- | --- |
| sCR | CR as defined below plus normal FLC ratio and absence of clonal cells in bone marrow by immunohistochemistry or immunofluorescence |

-continued

| Response | IMWG criteria |
| --- | --- |
| CR | Negative immunofixation on the serum and urine and disappearance of any soft tissue plasmacytomas and <5% plasma cells in bone marrow |
| VGPR | Serum and urine M-protein detectable by immunofixation but not on electrophoresis or ≥90% reduction in serum M-protein plus urine M-protein level <100 mg/24 h |
| PR | ≥50% reduction of serum M-protein and reduction in 24 hours urinary M-protein by ≥90% or to <200 mg/24 h<br>If the serum and urine M-protein are unmeasurable, 5 a ≥50% decrease in the difference between involved and uninvolved FLC levels is required in place of the M-protein criteria<br>If serum and urine M-protein are not measurable, and serum free light assay is also<br>not measureable, ≥50% reduction in plasma cells is required in place of M-protein,<br>provided baseline bone marrow plasma cell percentage was ≥30%<br>In addition to the above listed criteria, if present at baseline, a ≥50% reduction in the size of soft tissue plasmacytomas is also required |
| Stable Disease | Not meeting criteria for CR, VGPR, PR, or progressive disease |
| Progressive Disease | Increase of ≥25% from lowest response value in any one or more of the following:<br>Serum M-component and/or (the absolute increase must be ≥0.5 g/dL)6<br>Urine M-component and/or (the absolute increase must be ≥200 mg/24 h)<br>Only in patients without measurable serum and urine M-protein levels; the difference between involved and uninvolved FLC levels. The absolute increase must be >10 mg/dL<br>Bone marrow plasma cell percentage; the absolute percentage must be ≥10% 7<br>Definite development of new bone lesions or soft tissue plasmacytomas or definite increase in the size of existing bone lesions or soft tissue plasmacytomas<br>Development of hypercalcaemia (corrected serum calcium >11.5 mg/dL or 2.65 mmol/L) that can be attributed solely to the plasma cell proliferative disorder |
| Relapse | Clinical relapse requires one or more of:<br>Direct indicators of increasing disease and/or end organ dysfunction (CRAB features). It is<br>not used in calculation of time to progression or progression-free survival but is listed here as<br>something that can be reported optionally or for use in clinical practice<br>1. Development of new soft tissue plasmacytomas or bone lesions<br>2. Definite increase in the size of existing plasmacytomas or bone lesions. A definite increase is defined as a 50% (and at least 1 cm) increase as measured serially by the sum of the products of the cross-diameters of the measurable lesion<br>3. Hypercalcemia (>11.5 mg/dL) [2.65 mmol/L]<br>4. Decrease in haemoglobin of ≥2 g/dL [1.25 mmol/L]<br>5. Rise in serum creatinine by 2 mg/dL or more [177 mol/L or more] |

Electrophoresis is a method of separating proteins based on their biochemical properties. Serum is placed on a specific medium, and a charge is applied. The net charge (positive or negative) and the size and shape of the protein commonly are used in differentiating various serum proteins.

Several subsets of serum protein electrophoresis are available. The names of these subsets are based on the method that is used to separate and differentiate the various serum components. In zone electrophoresis, for example, different protein subtypes which are placed in separate physical locations on a gel made from agar, cellulose, or other plant material. The proteins are stained, and their densities are calculated electronically to provide graphical data on the absolute and relative amounts of the various proteins. Further separation of protein subtypes is achieved by staining with an immunologically active agent, which results in immunofixation and/or immunofluorescence.

The pattern of serum protein electrophoresis results depends on the fractions of two major types of proteins: albumin and globulins. Albumin, the major protein component of serum, is produced by the liver under normal physiologic conditions. Globulins comprise a smaller fraction of the total serum protein content. The subsets of these proteins and their relative quantity are mostly the primary focus of the interpretation of serum protein electrophoresis.

Albumin, the largest peak observed in serum protein electrophoresis, is located closest to the positive electrode. The next five components (globulins) are labeled alpha1, alpha2, beta1, beta2, and gamma. The peaks for these components appear toward the negative electrode, with the gamma peak being closest to that electrode.

Figure 3:
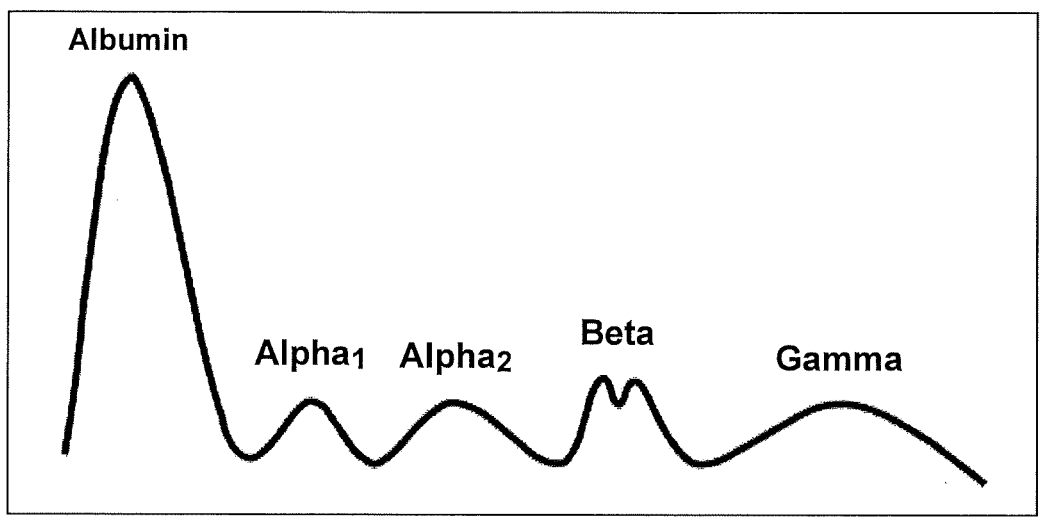
FIG. 3 shows a typical normal pattern for the distribution of proteins as determined by serum protein electrophoresis.

FIG. 3 shows a typical normal pattern for the distribution of proteins as determined by serum protein electrophoresis.

The albumin band represents the largest protein component of human serum. The albumin level is decreased under circumstances in which there is less production of the protein by the liver or in which there is increased loss or degradation of this protein. Malnutrition, significant liver disease, renal loss (e.g., in nephrotic syndrome), hormone therapy, and pregnancy may account for a low albumin level. Burns also may result in a low albumin level. Levels of albumin are increased for example in patients with a relative reduction in serum water (e.g., dehydration).

Moving toward the negative portion of the gel (i.e., the negative electrode), the next peaks involve the alpha1 and alpha2 components. The alpha1-protein fraction is comprised of alpha1-antitrypsin, thyroid-binding globulin, and transcortin. Malignancy and acute inflammation (resulting from acute-phase reactants) can increase the alpha1-protein band. A decreased alpha1-protein band may occur because of alpha1-antitrypsin deficiency or decreased production of the globulin as a result of liver disease. Ceruloplasmin, alpha2-macroglobulin, and haptoglobin contribute to the alpha2-protein band. The alpha2 component is increased as an acute-phase reactant.

The beta fraction has two peaks labeled beta1 and beta2. Beta1 is composed mostly of transferrin, and beta2 contains beta-lipoprotein. IgA, IgM, and sometimes IgG, along with complement proteins, also can be identified in the beta fraction.

Much of the clinical interest is focused on the gamma region of the serum protein spectrum because immunoglobulins migrate to this region. It should be noted that immunoglobulins often can be found throughout the electrophoretic spectrum. C-reactive protein (CRP) is located in the area between the beta and gamma components.

Figure 4:
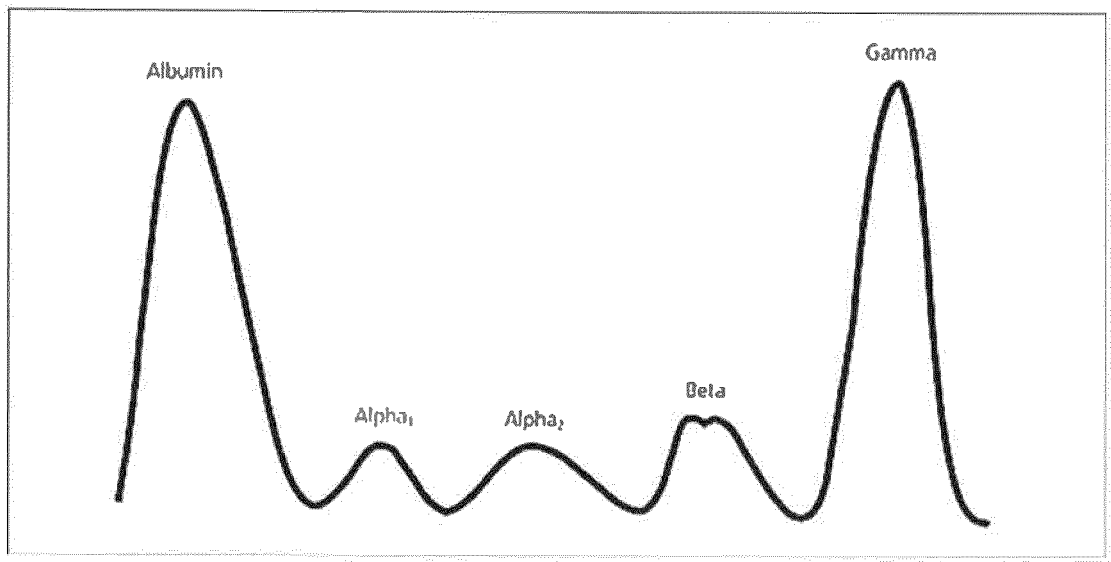
FIG. 4 shows a serum protein electrophoresis distribution of proteins having a homogeneous spike-like peak in a focal region of the gamma-globulin zone common to disorders known as monoclonal gammopathies. This peak represents a single clone of plasma cells that produce a homogeneous M protein.

Although many conditions can cause an increase in the gamma region, several disease states cause a homogeneous spike-like peak in a focal region of the gamma-globulin zone (FIG. 4). These so-called "monoclonal gammopathies" constitute a group of disorders that are characterized by proliferation of a single or very few clone(s) of plasma cells each producing a homogeneous M protein, such as MM.

Immunofixation electrophoresis (IFE) is a technique that allows a protein to be anchored after electrophoresis by forming an insoluble complex with a monoclonal or polyclonal detection antibody reagent added. It is performed in the following four steps:

1) Separation of proteins by electrophoresis.
2) Immunofixation (immunoprecipitation) of the electrophoresed proteins—the appropriate electrophoretic migration tracks are overlaid with individual antisera. The antisera diffuse into the gel and precipitate the corresponding antigens when present. The proteins in the reference track are fixed with a fixative agent.
3) The unprecipitated, soluble proteins are removed from the gel by blotting and washing. Precipitation of the antigen-antibody complex is trapped within the gel matrix.
4) The precipitated proteins are visualized by staining (e.g. acid violet stain).

To detect and identify the suspected monoclonal component, the sample is simultaneously electrophoresed in several tracks in parallel (see Figure). After the electrophoresis, the ELP track serves as a reference (containing the total protein fixation) providing a complete electrophoretic pattern of the serum sample's proteins. The remaining tracks allow characterization of the monoclonal component from its reaction, or lack of, usually with antisera against human IgG, IgA and IgM heavy chains, and against free and bound kappa and lambda light chains. Other anti-sera (e.g. anti-IgD, etc.) are also possible. The immunofixed bands are then compared with the suspect bands in the reference pattern—the corresponding band should have the same migration position.

Figure 5:
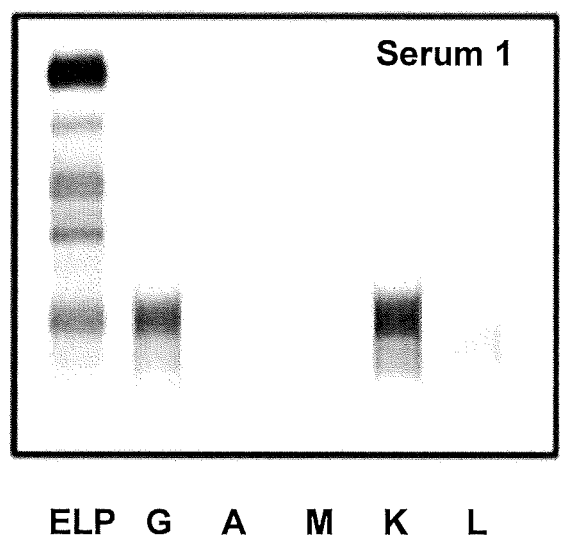
FIG. 5 shows an example of a gel after serum immunofixation electrophoresis of a healthy donor. Lane ELP=total protein staining; Lane G=anti-IgG staining; Lane A=anti-IgA staining; Lane M=anti-IgM staining; Lane K=anti-kappa staining; Lane L=anti-lambda staining.

FIG. 5 shows an example of a gel after serum immunofixation electrophoresis. A serum sample from a healthy donor was separated via gel electrophoresis 6 times in parallel whereas each lane was stained with a different reagent. After staining non complexed proteins were removed by blotting and washing. Lane ELP=total protein staining; Lane G=anti-IgG staining; Lane A=anti-IgA staining; Lane M=anti-IgM staining; Lane K=anti-kappa staining; Lane L=anti-lambda staining

WORKING EXAMPLES

Materials and Method IFE

Immunofixation was performed using Sebia's semi-automated agarose gel electrophoresis systems Hydrasys and Hydrasys2 and using Sebia's Maxikit Hydragel 9IF. The kits are designed for detection of Immunoglobulins in human serum by immunofixation electrophoresis and contain all needed reagents and materials i.e. agarose gels, buffered strips, diluent, acid violet stain, antisera (e.g. IgG, IgA, IgM, Kappa and Lambda), fixative solution and applicators.

Figure 6:
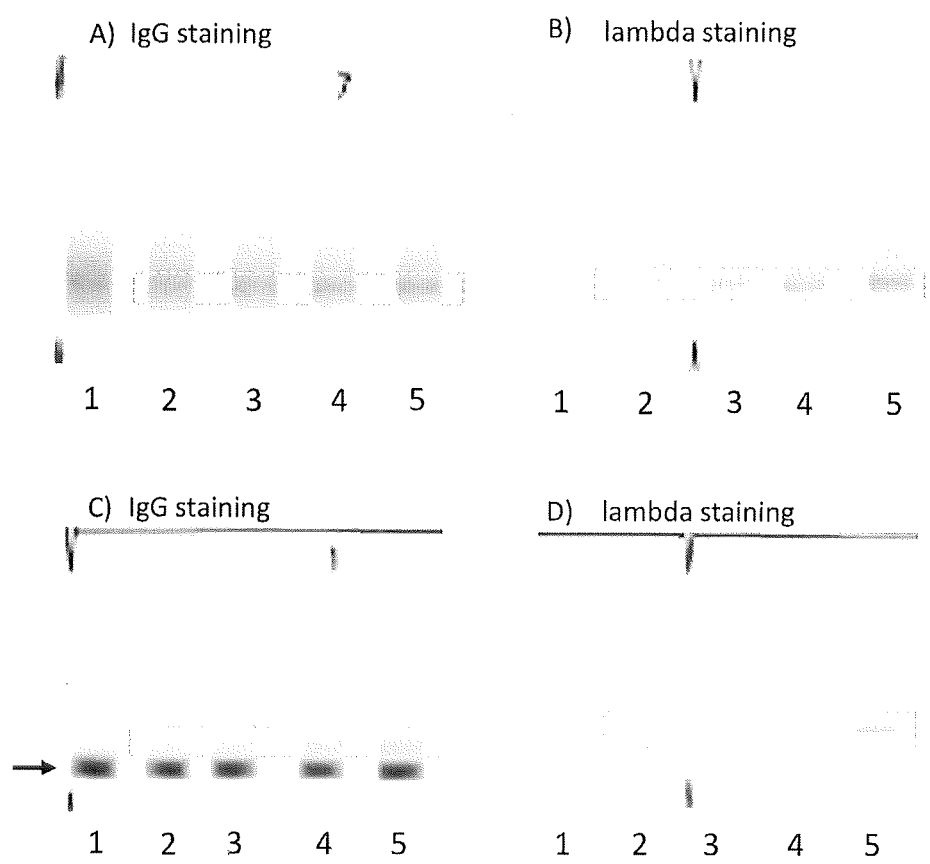
FIG. 6 shows a serum immunofixation electrophoresis of a sample from a drug naïve healthy donor (A and B) and a drug naive MM patient (C and D). The samples were tested either unspiked or spiked with MOR202 at different concentrations. (Lane 1=no MOR202 added; Lane 2=MOR202 added at 200 µg/mL; Lane 3=MOR202 added at 400 µg/mL; Lane 4=MOR202 added at 800 µg/mL; Lane 5=MOR202 added at 1200 µg/mL). Bands encircled with a dotted line become only visible after MOR202 spike and represent the respective molecule. Bands marked with an arrow represent endogenous M-protein.

In order to evaluate the impact of MOR202 on M-protein analysis, serum samples from healthy donors and MM patients were spiked with MOR202 at different concentrations and incubated for at least 15 min at room temperature (RT). Afterwards the samples were analyzed either spiked or unspiked with MOR202 using IFE and gels were stained with anti-IgG or anti-lambda antisera (both staining reagents are able to bind to MOR202). In both stainings MOR202 was detected already at the lowest concertation tested at 200 µg/mL suggesting IFE interference at or even below this drug serum level (FIG. 6).

In order to differentiate between MOR202 related assay signals in IFE vs. endogenous M-protein spikes a method was tested pre-incubating a MOR202 containing sample with an MOR202 specific anti-idiotypic antibody (MOR09292). The objective of this method was to demonstrate that the MOR202 related IFE assay signal can be migrated comparing samples with or without pre-incubation of MOR09292 and therefore clearly identifying MOR202 related assay signals. For evaluating if the migration distance is large enough to be detected samples containing MOR202 in saline were prepared and pre-incubated with or without MOR09292. The anti-idiotypic antibody was produced and tested in an IgG1 as well as in IgM antibody format. Test samples were prepared at a constant concentration of 1200 µg/mL MOR202 and pre-incubated without or with various concentrations of the two MOR09292 variants for 60 min. Afterwards, the samples were analyzed and IFE gels were stained with anti-IgG or anti-lambda antisera. The results were that no acceptable migration distance of the MOR202 drug spike suitable for clinical sample assessment could be observed when the test samples were pre-incubated with the various forms of MOR09292 (FIG. 7). The surprising finding demonstrate that even when increasing the size of the drug/antibody complex compared to the drug antibody alone approximately 3-fold (MOR09292-IgG) or 7-fold (MOR09292-IgM) the change in molecular weight of the complex does not lead to a relevant shift in assay signals (i.e. changed migration pattern).

Based on these results a further variant of the idiotypic antibody was generated genetically fusing MOR09292-Fab fragment to human albumin (MOR09292-hAlb). The new variant increased the size of the drug-antibody complex compared to the drug antibody alone up to 2.6-fold. More important the incorporation of human serum albumin lowered the overall net-charge of the complex. Sample preparation and testing was performed as described above. As a result a clear shift of the MOR202/MOR09292-huAlb complex could be observed when compared to the assay signal of MOR202 alone, see FIG. 8.

The modified IFE assay using MOR09292-hAlb for sample pre-treatment was incorporated into the clinical development of MOR202. Therefore, the assay was validated at the central laboratory responsible for M-protein analysis and introduced into the testing strategy as "Immunofixation (IFE) Reflex Assay". In order to discriminate between MOR202 and M-protein related signals the IFE Reflex Assay was performed in addition to the regular Serum IFE and Serum Protein Electrophoresis (SPE) for example when the following 2 conditions are fulfilled:
a) reduction in serum M-protein levels at least ≥40% compared to the M-protein concentration pre-treatment, and
b) at least one of the M-protein spikes left is identical to the characteristics of the drug antibody MOR202 (i.e. IgG/lambda positive staining in IFE).

Case Study for the Use and Results of the IFE Reflex Assay within Clinical Study MOR202C101

Within the first clinical study treating multiple myeloma patients with MOR202 (MOR202C101) the IFE Reflex Assay was applied for patient 19007 after a reduction of ≥86% in serum M-protein levels was observed. For this patient, the M-protein spike identified was described by IFE as IgG/lambda positive, the same molecular properties as known for MOR202. Performing SPE a remaining concentration of potential M-proteins at 1 or 2 g/L was detected on Jan. 12, 2106 and Feb. 19, 2016. The IFE Reflex Assay could demonstrate that this assay signal was solely caused by MOR202 interference and therefore not M-protein related (see summary laboratory results Table 1). The results demonstrate how the newly established IFE Reflex Assay could clearly discriminate between M-protein and therefore disease related assay signals versus MOR202 treatment related assay signals.

Table 1 IFE Reflex Assay Result Negative

TABLE 1

Case study for the clinical use of the modified IFE assay applying a MOR09292-hAlb sample pre-treatment step - summary laboratory report patient 19007
Before starting treatment with MOR202 patient 19007 was tested positive for serum M-protein (16 g/L for sample received Jul. 27, 2016 - positive staining for IgG/lambda in IFE).
After a ≥ 86% reduction in serum M-protein levels was observed (14-Dec 2015) the IFE Reflex assay was performed in addition to IFE and SPE. On Jan. 12, 2016 and Feb. 19, 2016 it was shown that the remaining M-protein concentration of 1 or 2 g/L, respectively, was only caused by MOR202 assay interference (i.e. Immunofixation Reflex Assay result "Negative" for M-proteins).

| | \multicolumn{11}{c}{Sample reception date} |
|---|---|---|---|---|---|---|---|---|---|---|---|
| | 19 Feb. 2016 | 11 JAN. 2016 | 14 DEC. 2015 | 16 NOV. 2015 | 26 OCT. 2015 | 21 SEP. 2015 | 07 SEP. 2015 | 24 AUG. 2015 | 10 AUG. 2015 | 27 JUL. 2015 | 17 JUL. 2015 |
| | \multicolumn{11}{c}{Visit} |
| | CYCLE 8/ DAY 1 | CYCLE 7/ DAY 1 | CYCLE 6/ DAY 1 | CYCLE 5/ DAY 1 | CYCLE 4/ DAY 8 | CYCLE 3/ DAY 1 | CYCLE 2/ DAY 15 | CYCLE 2/ DAY 1 | CYCLE 1/ DAY 15 | CYCLE 1/ DAY 1 | SCREENING |
| | \multicolumn{11}{c}{SERUM PROTEIN ELECTROPHORESIS} |
| Monoclonal peak 1 [Abs] | 2 | 1 | 2 | 2 | 2 | 3 | 4 | 6 | 9 | 16 | 15 |
| Unit | g/l | g/l | g/l | g/l | g/l | g/l | g/l | g/l | g/l | g/l | g/l |
| | \multicolumn{11}{c}{SERUM PROTEIN IMMUNOFIXATION} |
| Monoclonal peak 1 | IgG/l | IgG/l | IgG/l | IgG/l | IgG/l | IgG/l | IgG/l | IgG/l | IgG/l | IgG/l | IgG/l |
| | \multicolumn{11}{c}{Immunofix, Reflex Assay} |
| Monoclonal peak 1 | Negative | Negative | Positive | | | | | | | | |

Embodiments

An aspect is an anti-idiotypic antibody fused to albumin. In an embodiment, albumin is human albumin having the amino acid sequence of SEQ ID NO: 6. In an embodiment, the human albumin is a fragment of human albumin or partial sequence of human albumin.

In an embodiment, albumin is a functional fragment of albumin. In another embodiment, human albumin is a functional fragment of human albumin. In this context the term "functional fragment" of albumin or human albumin refers to albumin which is a fragment or a variant of native albumin or human albumin, but which still is functional active in a sense that it is still able to fulfill the physiological role of albumin.

An embodiment, is an anti-idiotypic antibody that is specific for an antibody having a variable heavy domain comprising the amino acid sequence (SEQ ID NO: 7)
QVQLVESGGGLVQPGGSLRLSCAASGFTFSSYYMNWVRQAPGKGLEWVSG

ISGDPSNTYYADSVKGRFTISRDNSKNTLYLQMNSLRAEDTAVYYCARDL

PLVYTGFAYWGQGTLVTVSS, and a variable light chain domain comprising the amino acid sequence (SEQ ID NO: 8)
DIELTQPPSVSVAPGQTARISCSGDNLRHYYVYWYQQKPGQAPVLVIYGD

SKRPSGIPERFSGSNSGNTATLTISGTQAEDEADYYCQTYTGGASLVFGG

GTKLTVLGQ.

An aspect, is an anti-idiotypic antibody that is specific for an antibody having a variable heavy domain comprising the amino acid sequence (SEQ ID NO: 7)
QVQLVESGGGLVQPGGSLRLSCAASGFTFSSYYMNWVRQAPGKGLEWVSG

ISGDPSNTYYADSVKGRFTISRDNSKNTLYLQMNSLRAEDTAVYYCARDL

PLVYTGFAYWGQGTLVTVSS, and a variable light chain domain comprising the amino acid sequence (SEQ ID NO: 8)
DIELTQPPSVSVAPGQTARISCSGDNLRHYYVYWYQQKPGQAPVLVIYGD

SKRPSGIPERFSGSNSGNTATLTISGTQAEDEADYYCQTYTGGASLVFGG

GTKLTVLGQ.

In an embodiment the anti-idiotypic antibody is fused to albumin. In an embodiment, albumin is human albumin having the amino acid sequence of SEQ ID NO: 6. In an embodiment, the human albumin is a fragment of human albumin or partial sequence of human albumin. In an embodiment, the human albumin is a functional fragment of human albumin or partial sequence of human albumin.

In embodiments, the anti-idiotypic antibody comprises a variable heavy chain comprising an HCDR1 of amino acid sequence
(SEQ ID NO: 18)
YSFSNYWIS, an HCDR2 of amino acid sequence
(SEQ ID NO: 19)
WMGIIDPASSKTRYSPSFQG, an HCDR3 of amino acid sequence
(SEQ ID NO: 20)
SRGAGMDY,
and a variable light chain comprising an LCDR1 of amino acid sequence
(SEQ ID NO: 21)
TGSSSNIGAGYDVH, an LCDR2 of amino acid sequence
(SEQ ID NO: 22)
LLIYADNNRPS, an LCDR3 of amino acid sequence
(SEQ ID NO: 23)
GSYDESSNSM.

In an embodiment, the anti-idiotypic antibody is a human antibody.

In embodiments, the anti-idiotypic antibody comprises the variable heavy chain of amino acid sequence (SEQ ID NO: 16)
QVQLVQSGAEVKKPGESLKISCKGSGYSFSNYWISWVRQMPGKGLEWMGI

IDPASSKTRYSPSFQGQVTISADKSISTAYLQWSSLKASDTAMYYCARSR

GAGMDYWGQGTLVTVSS, and
the variable light chain of amino acid sequence (SEQ ID NO: 17)
DIVLTQPPSVSGAPGQRVTISCTGSSSNIGAGYDVHWYQQLPGTAPKLLI

YADNNRPSGVPDRFSGSKSGTSASLAITGLQSEDEADYYCGSYDESSNSM

VFGGGTKLTVLGQ.

In embodiments, the anti-idiotypic antibody albumin fusion comprises the heavy chain amino acid sequence (SEQ ID NO: 24)
QVQLVQSGAEVKKPGESLKISCKGSGYSFSNYWISWVRQMPGKGLEWMGI

IDPASSKTRYSPSFQGQVTISADKSISTAYLQWSSLKASDTAMYYCARSR

GAGMDYWGQGTLVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKRVEPKSDIDAHKSEVAHRFKDLGEENFKALVLIAFAQ

YLQQCPFEDHVKLVNEVTEFAKTCVADESAENCDKSLHTLFGDKLCTVAT

LRETYGEMADCCAKQEPERNECFLQHKDDNPNLPRLVRPEVDVMCTAFHD

NEETFLKKYLYEIARRHPYFYAPELLFFAKRYKAAFTECCQAADKAACLL

PKLDELRDEGKASSAKQRLKCASLQKFGERAFKAWAVARLSQRFPKAEFA

EVSKLVTDLTKVHTECCHGDLLECADDRADLAKYICENQDSISSKLKECC

EKPLLEKSHCIAEVENDEMPADLPSLAADFVESKDVCKNYAEAKDVFLGM

FLYEYARRHPDYSVVLLLRLAKTYETTLEKCCAAADPHECYAKVFDEFKP

LVEEPQNLIKQNCELFEQLGEYKFQNALLVRYTKKVPQVSTPTLVEVSRN

LGKVGSKCCKHPEAKRMPCAEDYLSVVLNQLCVLHEKTPVSDRVTKCCTE

SLVNRRPCFSALEVDETYVPKEFNAETFTFHADICTLSEKERQIKKQTAL

VELVKHKPKATKEQLKAVMDDFAAFVEKCCKADDKETCFAEEGKKLVAAS

QAALGLVNSRHHHHHH.

In embodiments, the anti-idiotypic antibody albumin fusion comprises the light chain amino acid sequence (SEQ ID NO: 25)
DIVLTQPPSVSGAPGQRVTISCTGSSSNIGAGYDVHWYQQLPGTAPKLLI

YADNNRPSGVPDRFSGSKSGTSASLAITGLQSEDEADYYCGSYDESSNSM

VFGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS

An aspect is a method of evaluating a blood sample obtained from a patient undergoing treatment for multiple myeloma or other gammopathy comprising
e) obtaining a blood sample from said patient,
f) incubating the blood sample with an anti-idiotypic antibody,
g) performing immunofixation electrophoresis (IFE), and
h) reporting the results of the IFE.

In embodiments of the method, the patient is undergoing treatment with the antibody having a variable heavy domain comprising the amino acid sequence (SEQ ID NO: 7)
QVQLVESGGGLVQPGGSLRLSCAASGFTFSSYYMNWVRQAPGKGLEWVSG

ISGDPSNTYYADSVKGRFTISRDNSKNTLYLQMNSLRAEDTAVYYCARDL

PLVYTGFAYWGQGTLVTVSS, and
a variable light chain domain comprising the amino acid sequence (SEQ ID NO: 8)
DIELTQPPSVSVAPGQTARISCSGDNLRHYYVYWYQQKPGQAPVLVIYGD

SKRPSGIPERFSGSNSGNTATLTISGTQAEDEADYYCQTYTGGASLVFGG

GTKLTVLGQ.

In an embodiment of the method, the anti-idiotypic antibody is fused to albumin. In an embodiment of the method, albumin is human albumin having the amino acid sequence of SEQ ID NO: 6. In an embodiment of the method, the human albumin is a fragment of human albumin or partial sequence of human albumin.

The exemplified anti-idiotypic antibody MOR09292 is specific for MOR202. The anti-idiotypic antibody to MOR202, when fused to human albumin, shifted the antibody in IFE thus mitigating any potential interference of MOR202 with the M-protein based clinical assessment. It is expected that the fusion of other anti-idiotypic antibody that our specific for other antibodies that are used for therapy in multiple myeloma or other gammopathy would have a similar result. Meaning that other anti-idiotypic antibody albumin fusions would be useful in shifting the antibody in IFE thus mitigating any potential interference of that antibody with the M-protein based clinical assessment.

In embodiments of the method, the anti-idiotypic antibody comprises a variable heavy chain comprising

```
an HCDR1 of amino acid sequence
                              (SEQ ID NO: 18)
YSFSNYWIS, an HCDR2 of amino acid sequence
                              (SEQ ID NO: 19)
WMGIIDPASSKTRYSPSFQG, an HCDR3 of amino acid sequence
                              (SEQ ID NO: 20)
SRGAGMDY,
and a variable light chain comprising an LCDR1 of amino acid sequence
                              (SEQ ID NO: 21)
TGSSSNIGAGYDVH, an LCDR2 of amino acid sequence
                              (SEQ ID NO: 22)
LLIYADNNRPS, an LCDR3 of amino acid sequence
                              (SEQ ID NO: 23)
GSYDESSNSM.
```

In embodiments of the method, the anti-idiotypic antibody is a human antibody.

In embodiments of the method, the anti-idiotypic antibody comprises the variable heavy chain of amino acid sequence

```
                              (SEQ ID NO: 16)
QVQLVQSGAEVKKPGESLKISCKGSGYSFSNYWISWVRQMPGKGLEWMGI

IDPASSKTRYSPSFQGQVTISADKSISTAYLQWSSLKASDTAMYYCARSR

GAGMDYWGQGTLVTVSS,
``` and
the variable light chain of amino acid sequence

```
                              (SEQ ID NO: 17)
DIVLTQPPSVSGAPGQRVTISCTGSSSNIGAGYDVHWYQQLPGTAPKLLI

YADNNRPSGVPDRFSGSKSGTSASLAITGLQSEDEADYYCGSYDESSNSM

VFGGGTKLTVLGQ.
```

In embodiments of the method, the anti-idiotypic antibody albumin fusion comprises the heavy chain amino acid sequence

```
                              (SEQ ID NO: 24)
QVQLVQSGAEVKKPGESLKISCKGSGYSFSNYWISWVRQMPGKGLEWMGI

IDPASSKTRYSPSFQGQVTISADKSISTAYLQWSSLKASDTAMYYCARSR

GAGMDYWGQGTLVTVSSASTKGPSVFPLAPSSKSTSGGTAALGCLVKDYF
```

```
                              -continued
PEPVTVSWNSGALTSGVHTFPAVLQSSGLYSLSSVVTVPSSSLGTQTYIC

NVNHKPSNTKVDKRVEPKSDIDAHKSEVAHRFKDLGEENFKALVLIAFAQ

YLQQCPFEDHVKLVNEVTEFAKTCVADESAENCDKSLHTLFGDKLCTVAT

LRETYGEMADCCAKQEPERNECFLQHKDDNPNLPRLVRPEVDVMCTAFHD

NEETFLKKYLYEIARRHPYFYAPELLFFAKRYKAAFTECCQAADKAACLL

PKLDELRDEGKASSAKQRLKCASLQKFGERAFKAWAVARLSQRFPKAEFA

EVSKLVTDLTKVHTECCHGDLLECADDRADLAKYICENQDSISSKLKECC

EKPLLEKSHCIAEVENDEMPADLPSLAADFVESKDVCKNYAEAKDVFLGM

FLYEYARRHPDYSVVLLLRLAKTYETTLEKCCAAADPHECYAKVFDEFKP

LVEEPQNLIKQNCELFEQLGEYKFQNALLVRYTKKVPQVSTPTLVEVSRN

LGKVGSKCCKHPEAKRMPCAEDYLSVVLNQLCVLHEKTPVSDRVTKCCTE

SLVNRRPCFSALEVDETYVPKEFNAETFTFHADICTLSEKERQIKKQTAL

VELVKHKPKATKEQLKAVMDDFAAFVEKCCKADDKETCFAEEGKKLVAAS

QAALGLVNSRHHHHHH.
```

In embodiments of the method, the anti-idiotypic antibody albumin fusion comprises the light chain amino acid sequence

```
                              (SEQ ID NO: 25)
DIVLTQPPSVSGAPGQRVTISCTGSSSNIGAGYDVHWYQQLPGTAPKLLI

YADNNRPSGVPDRFSGSKSGTSASLAITGLQSEDEADYYCGSYDESSNSM

VFGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS
```

In embodiments of the method, the sample is obtained from a patient undergoing treatment for multiple myeloma or other gammopathy. In further embodiments, the gammopathy is a monoclonal gammopathy. In further embodiments, the monoclonal gammopathies include: Hodgkin's disease; variants of multiple myeloma, e.g., Solitary plasmacytoma of bone, Extramedullary plasmacytoma, Plasma cell leukemia, and Non-secretory myeloma, Lymphoproliferative disorders, such as, Waldenström's macroglobulinemia, and Lymphoma; Heavy chain disease (γ, α, μ); and Amyloidosis.

In embodiments of the method, the sample is evaluated for total M-protein levels.

An aspect, is a nucleic acid encoding the exemplified anti-idiotypic antibody or anti-idiotypic antibody albumin fusion. In an embodiment, the anti-idiotypic antibody is MOR09292. In an embodiment the anti-idiotypic antibody is encoded by nucleic acid sequences encoding the amino acid sequences shown in FIGS. 2A-B.

In an embodiment the anti-idiotypic antibody is encoded by nucleic acid sequences SEQ ID NO: 26 (VH) and SEQ ID NO: 27 (VL).

The invention claimed is:

1. A monoclonal anti-idiotypic antibody fused to albumin, wherein the monoclonal anti-idiotypic antibody is specific for a therapeutic antibody specific for CD38, and wherein the monoclonal anti-idiotypic antibody comprises a variable heavy chain comprising
an HCDR1 comprising the amino acid sequence of SEQ ID NO: 18,
an HCDR2 comprising the amino acid sequence of SEQ ID NO: 19, and
an HCDR3 comprising the amino acid sequence of SEQ ID NO: 20, and
a variable light chain comprising
an LCDR1 comprising the amino acid sequence of SEQ ID NO: 21,
an LCDR2 comprising the amino acid sequence of SEQ ID NO: 22, and
an LCDR3 comprising the amino acid sequence of SEQ ID NO: 23.

2. The monoclonal anti-idiotypic antibody fused to albumin according to claim 1, wherein the monoclonal anti-idiotypic antibody comprises a variable heavy chain comprising the amino acid sequence of SEQ ID NO: 16, and a variable light chain comprising the amino acid sequence of SEQ ID NO: 17.

3. The monoclonal anti-idiotypic antibody fused to albumin fusion according to claim 1 comprising a heavy chain comprising the heavy chain amino acid sequence of SEQ ID NO: 24; and
a light chain comprising the light chain amino acid sequence of SEQ ID NO: 25.

4. The monoclonal anti-idiotypic antibody fused to albumin according to claim 1, wherein the anti-idiotypic antibody is an IgG1 isotype.

5. The monoclonal anti-idiotypic antibody fused to albumin according to claim 1, wherein the anti-idiotypic antibody is an IgM isotype.

6. The monoclonal anti-idiotypic antibody fused to albumin according to claim 1, wherein the albumin is a human albumin having the amino acid sequence of SEQ ID NO: 6.

\* \* \* \* \*

SEQUENCE LISTING

<160> NUMBER OF SEQ ID NOS: 28

<210> SEQ ID NO 1
<211> LENGTH: 300
<212> TYPE: PRT
<213> ORGANISM: Homo sapiens

<400> SEQUENCE: 1

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Pro Arg Trp Arg Gln
        35                  40                  45

Gln Trp Ser Gly Pro Gly Thr Thr Lys Arg Phe Pro Glu Thr Val Leu
50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
            85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
            115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
            195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
            275                 280                 285

Lys Asn Pro Glu Asp Ser Ser Cys Thr Ser Glu Ile
290                 295                 300

<210> SEQ ID NO 2
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

```
<400> SEQUENCE: 2
caggtgcaat tggtggaaag cggcggcggc ctggtgcaac cgggcggcag cctgcgtctg    60
agctgcgcgg cctccggatt taccttttct tcttattata tgaattgggt gcgccaagcc   120
cctgggaagg gtctcgagtg ggtgagcggt atctctggtg atcctagcaa tacctattat   180
gcggatagcg tgaaaggccg ttttaccatt tcacgtgata attcgaaaaa caccctgtat   240
ctgcaaatga acagcctgcg tgcggaagat acggccgtgt attattgcgc gcgtgatctt   300
cctcttgttt atactggttt tgcttattgg ggccaaggca ccctggtgac ggttagctca   360
```

```
<210> SEQ ID NO 3
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3
gatatcgaac tgacccagcc gccttcagtg agcgttgcac caggtcagac cgcgcgtatc    60
tcgtgtagcg gcgataatct tcgtcattat tatgtttatt ggtaccagca gaaacccggg   120
caggcgccag ttcttgtgat ttatggtgat tctaagcgtc cctcaggcat cccggaacgc   180
tttagcggat ccaacagcgg caacaccgcg accctgacca ttagcggcac tcaggcggaa   240
gacgaagcgg attattattg ccagacttat actggtggtg cttctcttgt gtttggcggc   300
ggcacgaagt taaccgttct tggccag                                       327
```

```
<210> SEQ ID NO 4
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4
caggtgcaat tggttcagag cggcgcggaa gtgaaaaaac cgggcgaaag cctgaaaatt    60
agctgcaaag gttccggata ttcctttttct aattattgga tttcttgggt gcgccagatg   120
cctgggaagg gtctcgagtg gatgggcatt atcgatccgg cttctagcaa gacccgttat   180
tctccgagct ttcagggcca ggtgaccatt agcgcggata aaagcattag caccgcgtat   240
cttcaatgga gcagcctgaa agcgagcgat acggccatgt attattgcgc gcgttctcgt   300
ggtgctggta tggattattg gggccaaggc accctggtga cggttagctc a           351
```

```
<210> SEQ ID NO 5
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5
gatatcgtgc tgacccagcc gccttcagtg agtggcgcac caggtcagcg tgtgaccatc    60
tcgtgtacgg gcagcagcag caacattggt gctggttatg atgtgcattg gtaccagcag   120 ttgccccggga cggcgccgaa acttctgatt tatgctgata ataatcgtcc ctcaggcgtg   180
```

```
ccggatcgtt ttagcggatc caaaagcggc accagcgcga gccttgcgat tacgggcctg    240
caaagcgaag acgaagcgga ttattattgc ggttcttatg atgagtcttc taattctatg    300
gtgtttggcg gcggcacgaa gttaaccgtt cttggccag                           339
```

<210> SEQ ID NO 6
<211> LENGTH: 609
<212> TYPE: PRT
<213> ORGANISM: Homo sapiens

<400> SEQUENCE: 6

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350
```

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Leu Glu Lys Cys
370                 375                 380

Cys Ala Ala Ala Asp Pro His Glu Cys Tyr Ala Lys Val Phe Asp Glu
385                 390                 395                 400

Phe Lys Pro Leu Val Glu Pro Gln Asn Leu Ile Lys Gln Asn Cys
            405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
            450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
            485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
            530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
            565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
            595                 600                 605

Leu

<210> SEQ ID NO 7
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Gly Ile Ser Gly Asp Pro Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
        115                 120

<210> SEQ ID NO 8
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg His Tyr Tyr Val
            20                  25                  30

Tyr Trp Tyr Gln Gln Lys Pro Gly Gln Ala Pro Val Leu Val Ile Tyr
            35                  40                  45

Gly Asp Ser Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Gly Gly Ala Ser Leu
            85                  90                  95

Val Phe Gly Gly Gly Thr Lys Leu Thr Val Leu Gly Gln
            100                 105

<210> SEQ ID NO 9
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Phe Thr Phe Ser Ser Tyr Tyr Met Asn
1               5                   10

<210> SEQ ID NO 10
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Ser Tyr Tyr Met Asn
1               5

<210> SEQ ID NO 11
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 11

Gly Ile Ser Gly Asp Pro Ser Asn Thr Tyr Tyr Ala Asp Ser Val Lys
1               5                   10                  15

Gly

<210> SEQ ID NO 12
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Asp Leu Pro Leu Val Tyr Thr Gly Phe Ala Tyr
1               5                   10

<210> SEQ ID NO 13
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ser Gly Asp Asn Leu Arg His Tyr Tyr Val Tyr
1               5                   10

<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gly Asp Ser Lys Arg Pro Ser
1               5

<210> SEQ ID NO 15
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gln Thr Tyr Thr Gly Gly Ala Ser
1               5

<210> SEQ ID NO 16
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 16

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Ser Trp Val Arg Gln Met Pro Gly Lys Gly Leu Glu Trp Met
        35                  40                  45

Gly Ile Ile Asp Pro Ala Ser Ser Lys Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Arg Gly Ala Gly Met Asp Tyr Trp Gly Gln Gly Thr Leu
            100                 105                 110

Val Thr Val Ser Ser
        115

<210> SEQ ID NO 17
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Asp Ile Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ala Asp Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Gly Ser Tyr Asp Glu Ser
                85                  90                  95

Ser Asn Ser Met Val Phe Gly Gly Thr Lys Leu Thr Val Leu Gly
            100                 105                 110

Gln

<210> SEQ ID NO 18
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Tyr Ser Phe Ser Asn Tyr Trp Ile Ser
1               5

-continued

```
<210> SEQ ID NO 19
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Trp Met Gly Ile Ile Asp Pro Ala Ser Ser Lys Thr Arg Tyr Ser Pro
1               5                   10                  15

Ser Phe Gln Gly
            20

<210> SEQ ID NO 20
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ser Arg Gly Ala Gly Met Asp Tyr
1               5

<210> SEQ ID NO 21
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Thr Gly Ser Ser Ser Asn Ile Gly Ala Gly Tyr Asp Val His
1               5                   10

<210> SEQ ID NO 22
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Leu Leu Ile Tyr Ala Asp Asn Asn Arg Pro Ser
1               5                   10

<210> SEQ ID NO 23
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Gly Ser Tyr Asp Glu Ser Ser Asn Ser Met
1               5                   10
```

```
<210> SEQ ID NO 24
<211> LENGTH: 816
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24
```

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Ser Trp Val Arg Gln Met Pro Gly Lys Gly Leu Glu Trp Met
        35                  40                  45

Gly Ile Ile Asp Pro Ala Ser Ser Lys Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Arg Gly Ala Gly Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Asp Ile Asp Ala His
    210                 215                 220

Lys Ser Glu Val Ala His Arg Phe Lys Asp Leu Gly Glu Glu Asn Phe
225                 230                 235                 240

Lys Ala Leu Val Leu Ile Ala Phe Ala Gln Tyr Leu Gln Gln Cys Pro
                245                 250                 255

Phe Glu Asp His Val Lys Leu Val Asn Glu Val Thr Glu Phe Ala Lys
            260                 265                 270

Thr Cys Val Ala Asp Glu Ser Ala Glu Asn Cys Asp Lys Ser Leu His
        275                 280                 285

Thr Leu Phe Gly Asp Lys Leu Cys Thr Val Ala Thr Leu Arg Glu Thr
    290                 295                 300

Tyr Gly Glu Met Ala Asp Cys Cys Ala Lys Gln Glu Pro Glu Arg Asn
305                 310                 315                 320

Glu Cys Phe Leu Gln His Lys Asp Asp Asn Pro Asn Leu Pro Arg Leu
                325                 330                 335

Val Arg Pro Glu Val Asp Val Met Cys Thr Ala Phe His Asp Asn Glu
            340                 345                 350

Glu Thr Phe Leu Lys Lys Tyr Leu Tyr Glu Ile Ala Arg Arg His Pro
        355                 360                 365

-continued

| | | | | | | | | | | | | |
|---|---|---|---|---|---|---|---|---|---|---|---|---|
|Tyr|Phe|Tyr|Ala|Pro|Glu|Leu|Leu|Phe|Phe|Ala|Lys|Arg|Tyr|Lys|Ala|
|370| | | | |375| | | | |380| | | | | |

Ala Phe Thr Glu Cys Cys Gln Ala Ala Asp Lys Ala Ala Cys Leu Leu
385                     390                     395                     400

Pro Lys Leu Asp Glu Leu Arg Asp Gly Lys Ala Ser Ser Ala Lys
                405                     410                     415

Gln Arg Leu Lys Cys Ala Ser Leu Gln Lys Phe Gly Glu Arg Ala Phe
                420                     425                     430

Lys Ala Trp Ala Val Ala Arg Leu Ser Gln Arg Phe Pro Lys Ala Glu
                435                     440                     445

Phe Ala Glu Val Ser Lys Leu Val Thr Asp Leu Thr Lys Val His Thr
450                     455                     460

Glu Cys Cys His Gly Asp Leu Leu Glu Cys Ala Asp Asp Arg Ala Asp
465                     470                     475                     480

Leu Ala Lys Tyr Ile Cys Glu Asn Gln Asp Ser Ile Ser Ser Lys Leu
                485                     490                     495

Lys Glu Cys Cys Glu Lys Pro Leu Leu Glu Lys Ser His Cys Ile Ala
                500                     505                     510

Glu Val Glu Asn Asp Glu Met Pro Ala Asp Leu Pro Ser Leu Ala Ala
                515                     520                     525

Asp Phe Val Glu Ser Lys Asp Val Cys Lys Asn Tyr Ala Glu Ala Lys
530                     535                     540

Asp Val Phe Leu Gly Met Phe Leu Tyr Glu Tyr Ala Arg Arg His Pro
545                     550                     555                     560

Asp Tyr Ser Val Val Leu Leu Leu Arg Leu Ala Lys Thr Tyr Glu Thr
                565                     570                     575

Thr Leu Glu Lys Cys Cys Ala Ala Ala Asp Pro His Glu Cys Tyr Ala
                580                     585                     590

Lys Val Phe Asp Glu Phe Lys Pro Leu Val Glu Glu Pro Gln Asn Leu
                595                     600                     605

Ile Lys Gln Asn Cys Glu Leu Phe Glu Gln Leu Gly Glu Tyr Lys Phe
                610                     615                     620

Gln Asn Ala Leu Leu Val Arg Tyr Thr Lys Lys Val Pro Gln Val Ser
625                     630                     635                     640

Thr Pro Thr Leu Val Glu Val Ser Arg Asn Leu Gly Lys Val Gly Ser
                645                     650                     655

Lys Cys Cys Lys His Pro Glu Ala Lys Arg Met Pro Cys Ala Glu Asp
                660                     665                     670

Tyr Leu Ser Val Val Leu Asn Gln Leu Cys Val Leu His Glu Lys Thr
                675                     680                     685

Pro Val Ser Asp Arg Val Thr Lys Cys Cys Thr Glu Ser Leu Val Asn
                690                     695                     700

Arg Arg Pro Cys Phe Ser Ala Leu Glu Val Asp Glu Thr Tyr Val Pro
705                     710                     715                     720

Lys Glu Phe Asn Ala Glu Thr Phe Thr Phe His Ala Asp Ile Cys Thr
                725                     730                     735

Leu Ser Glu Lys Glu Arg Gln Ile Lys Lys Gln Thr Ala Leu Val Glu
                740                     745                     750

Leu Val Lys His Lys Pro Lys Ala Thr Lys Glu Gln Leu Lys Ala Val
                755                     760                     765

Met Asp Asp Phe Ala Ala Phe Val Glu Lys Cys Cys Lys Ala Asp Asp
770                     775                     780

```
Lys Glu Thr Cys Phe Ala Glu Glu Gly Lys Lys Leu Val Ala Ala Ser
785                 790                 795                 800

Gln Ala Ala Leu Gly Leu Val Asn Ser Arg His His His His His His
            805                 810                 815
```

<210> SEQ ID NO 25
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 25

```
Asp Ile Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Ala Asp Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ser Glu Asp Glu Ala Asp Tyr Tyr Cys Gly Ser Tyr Asp Glu Ser
                85                  90                  95

Ser Asn Ser Met Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215
```

<210> SEQ ID NO 26
<211> LENGTH: 2448
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26

```
caggtgcaat tggttcagag cggcgcggaa gtgaaaaaac cgggcgaaag cctgaaaatt      60
agctgcaaag gttccggata ttccttttct aattattgga tttcttgggt gcgccagatg     120
cctgggaagg gtctcgagtg gatgggcatt atcgatccgg cttctagcaa gacccgttat     180
tctccgagct ttcagggcca ggtgaccatt agcgcggata aaagcattag caccgcgtat     240
```

```
cttcaatgga gcagcctgaa agcgagcgat acggccatgt attattgcgc gcgttctcgt      300
ggtgctggta tggattattg gggccaaggc accctggtga cggttagctc agcctccacc      360
aagggtccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga gagttgagcc caaatctgat      660
atcgacgccc acaagagcga ggtggcccac cggtttaagg acctgggcga ggaaaacttc      720
aaggccctgg tgctgatcgc cttcgcccag tacctgcagc agtgcccctt cgaggaccac      780
gtgaagctcg tgaacgaagt gaccgagttc gccaagacct gcgtggccga tgagagcgcc      840
gagaactgcg acaagagcct gcacaccctg ttcggcgaca agctgtgtac cgtggccacc      900
ctgagagaaa cctacggcga gatggccgac tgctgcgcca gcaggaacc cgagaggaac       960
gagtgcttcc tgcagcacaa ggacgacaac cccaacctgc ccagactcgt gcggcccgaa     1020
gtggacgtga tgtgcaccgc cttccacgac aacgaggaaa ccttcctgaa gaagtacctg     1080
tacgagatcg ccagacggca cccctacttc tacgcccccg agctgctgtt cttcgccaag     1140
cggtacaagg ccgccttcac cgagtgttgc caggccgccg ataaggccgc ttgcctgctg     1200
cctaagctgg acgagctgag ggatgagggc aaggccagct ctgccaagca gagactgaag     1260
tgcgccagcc tgcagaagtt cggcgagcgg gcctttaaag cctgggccgt ggctagactg     1320
agccagagat cccccaaggc cgagtttgcc gaggtgtcca agctcgtgac cgacctgacc     1380
aaggtgcaca ccgagtgctg tcacggcgac ctgctggaat gcgccgacga cagagccgat     1440
ctggccaagt acatctgcga gaaccaggac agcatcagca gcaagctgaa agagtgctgc     1500
gagaagcctc tgctggaaaa gagccactgt atcgccgagg tggaaaacga cgagatgccc     1560
gccgatctgc cttctctggc cgccgacttc gtggaaagca aggacgtgtg caagaactac     1620
gccgaggcca aggatgtgtt cctgggcatg tttctgtatg agtacgcccg cagacacccc     1680
gactacagcg tggtgctgct gctgagactg gccaaaacct acgagacaac cctggaaaag     1740
tgctgtgccg ccgctgaccc ccacgagtgt tacgccaagg tgttcgacga gttcaagcca     1800
ctggtggaag accccagaa cctgatcaag cagaattgcg agctgttcga gcagctgggc     1860
gagtacaagt ccagaacgc cctgctcgtg cggtacacca gaaagtgcc ccaggtgtcc      1920
accccacc tggtggaagt gtcccggaac ctgggcaaag tgggcagcaa gtgctgcaag     1980
caccctgagg ccaagagaat gccctgcgcc gaggactacc tgtctgtggt gctgaaccag     2040
ctgtgcgtgc tgcacgagaa aacccccgtg tccgacagag tgaccaagtg ctgtaccgag     2100
agcctcgtga acagacggcc ctgcttcagc gccctggaag tggatgagac atacgtgccc     2160
aaagagttca acgccgagac attccacttc cacgccgaca tctgcaccct gtccgagaaa     2220
gagcggcaga tcaagaaaca gaccgctctg gtggaactcg tgaagcacaa gcccaaggcc     2280
accaaagaac agctgaaggc cgtgatggac gacttcgccg cctttgtgga aaaatgctgc     2340
aaggccgatg acaaagagac atgcttcgcc gaagagggca gaaactggt ggccgcctct     2400
caggctgctc tgggactggt taactctaga caccatcacc atcaccat              2448
```

<210> SEQ ID NO 27
<211> LENGTH: 651
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 27
gatatcgtgc tgacccagcc gccttcagtg agtggcgcac caggtcagcg tgtgaccatc        60
tcgtgtacgg gcagcagcag caacattggt gctggttatg atgtgcattg gtaccagcag       120
ttgcccggga cggcgccgaa acttctgatt tatgctgata ataatcgtcc ctcaggcgtg       180
ccggatcgtt ttagcggatc caaaagcggc accagcgcga gccttgcgat tacgggcctg       240
caaagcgaag acgaagcgga ttattattgc ggttcttatg atgagtcttc taattctatg       300
gtgtttggcg gcggcacgaa gttaaccgtc ctaggtcagc ccaaggctgc cccctcggtc       360
actctgttcc cgccctcctc tgaggagctt caagccaaca aggccacact ggtgtgtctc       420
ataagtgact tctacccggg agccgtgaca gtggcctgga aggcagatag cagccccgtc       480
aaggcgggag tggagaccac cacaccctcc aaacaaagca acaacaagta cgcggccagc       540
agctatctga gcctgacgcc tgagcagtgg aagtcccaca gaagctacag ctgccaggtc       600
acgcatgaag ggagcaccgt ggagaagaca gtggccccta cagaatgttc a               651

<210> SEQ ID NO 28
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 28

His His His His His His
1               5
```